US012732761B2

(12) United States Patent
McCreery et al.

(10) Patent No.: US 12,732,761 B2
(45) Date of Patent: Sep. 8, 2026

(54) PREDICTING REAL-EAR-TO-COUPLER DIFFERENCES BASED ON CLINICAL IMMITTANCE MEASURES OF THE MIDDLE EAR

(71) Applicant: Father Flanagan's Boys' Home, Omaha, NE (US)

(72) Inventors: Ryan McCreery, Omaha, NE (US); Gabrielle Merchant, Omaha, NE (US); Jeff Crukley, Milton (CA)

(73) Assignee: Father Flanagan's Boys' Home, Omaha, NE (US)

( * ) Notice: Subject to any disclaimer, the term of this patent is extended or adjusted under 35 U.S.C. 154(b) by 298 days.

(21) Appl. No.: 18/449,844

(22) Filed: Aug. 15, 2023

(65) Prior Publication Data

US 2024/0056749 A1 Feb. 15, 2024

Related U.S. Application Data

(60) Provisional application No. 63/371,441, filed on Aug. 15, 2022.

(51) Int. Cl.
*H04R 25/00* (2006.01)
*A61B 5/12* (2006.01)
*H04R 29/00* (2006.01)

(52) U.S. Cl.
CPC ............. *H04R 25/70* (2013.01); *A61B 5/126* (2013.01); *H04R 25/507* (2013.01); *H04R 29/00* (2013.01)

(58) Field of Classification Search
CPC ................................ A61B 5/126; H04R 25/70
See application file for complete search history.

(56) References Cited

U.S. PATENT DOCUMENTS

2013/0303941 A1 11/2013 Porges et al.
2016/0112814 A1* 4/2016 Hug ...................... H04R 25/70 381/60

(Continued)

FOREIGN PATENT DOCUMENTS

WO WO-2019238801 A1 * 12/2019 ............ H04R 25/30

OTHER PUBLICATIONS

"American Academy of Audiology Clinical Practice Guidelines on Pediatric Amplification," American Academy of Audiology, Jun. 2013, 60 pages.

(Continued)

*Primary Examiner* — Carolyn R Edwards
*Assistant Examiner* — Dylan Maguire Neece
(74) *Attorney, Agent, or Firm* — McKee, Voorhees & Sease, PLC

(57) ABSTRACT

Pediatric hearing-aid verification relies on probe microphone measures of output from the ear canal or in a coupler with the child's real-ear-to-coupler difference (RECD). These measures cannot always be completed in children, leading to inaccuracies in fitting when average RECD values are used instead. Audiologists often have tympanometry data that characterizes the impedance of outer and middle ear. Creating a machine-learned model to train itself to incorporate and refine the modelling such as by incorporating clinical tympanometric data into predictions of individual RECDs led to more accurate estimates and smaller errors than using age-based average RECD alone. The modelling can be included in clinical diagnostic tools to quickly and non-invasively provide improved estimation for pediatric hearing-aid verification in a clinical setting.

13 Claims, 15 Drawing Sheets

(56) References Cited

U.S. PATENT DOCUMENTS

2016/0183012 A1* 6/2016 Pedersen ............. H04R 25/554 381/318
2020/0315544 A1* 10/2020 Levine ................ A61B 5/6898

OTHER PUBLICATIONS

"Electroacoustics—Simulators of human head and ear—Part 5: 2 cm3 coupler for the measurement of hearing aids and earphones coupled to the ear by means of ear inserts," British Standards, Sep. 2006, 18 pages.
Aarts et al., "Manufacturer predicted and measured REAR values in adult hearing aid fitting: accuracy and clinical usefulness," International Journal of Audiology, May 2005, vol. 44, No. 5, pp. 293-301.
Aazh et al., "The accuracy of matching target insertion gains with open-fit hearing aids," American Journal of Audiology, Dec. 2012, vol. 21, pp. 175-180.
Alaerts et al., "Evaluation of middle ear function in young children: clinical guidelines for the use of 226- and 1,000-Hz tympanometry," Otology & Neurotology, Sep. 2007, vol. 28, No. 6, pp. 727-732.
Bagatto et al., "Clinical protocols for hearing instrument fitting in the Desired Sensation Level method," Trends In Amplification, 2005, vol. 9, No. 4, pp. 199-226.
Bagatto et al., "Prescribing and Verifying Hearing Aids Applying the American Academy of Audiology Pediatric Amplification Guideline: Protocols and Outcomes from the Ontario Infant Hearing Program," Journal of the American Academy of Audiology, Mar. 2016, vol. 27, No. 3, pp. 188-203.
Bagatto et al., "Protocol for the provision of amplification," Version 2019, National Centre for Audiology, Mar. 2019, pp. 1-100.
Barlow et al., "Probe-tube microphone measures in hearing-impaired children and adults," Ear and Hearing, Oct. 1988, vol. 9, No. 5, pp. 243-247.
Blumsack et al., "Alternative metrics for real-ear-to-coupler difference average values in children," Journal of the American Academy of Audiology, Oct. 2014, vol. 25, No. 9, pp. 823-833.
Burkner, Paul-Christian, "Advanced Bayesian multilevel modeling with the R package brms," The R Journal, Jul. 2018, vol. 10, No. 1, pp. 395-411.
Burkner, Paul-Christian, "brms: An R package for Bayesian multilevel models using Stan," Journal of Statistical Software, Aug. 2017, vol. 80, No. 1, 28 pages.
Carpenter et al., "Stan: A Probabilistic Programming Language," Journal of Statistical Software, Jan. 2017, vol. 76, No. 1, 32 pages.
Chan et al., "Estimation of eardrum acoustic pressure and of ear canal length from remote points in the canal," Journal of the Acoustical Society of America, Mar. 1990, vol. 87, No. 3, pp. 1237-1247.
Ching et al., "Introduction to the longitudinal outcomes of children with hearing impairment (LOCHI) study: background, design, sample characteristics," International Journal of Audiology, Dec. 2013, vol. 52, pp. S4-S9.
Cicchetti, Domenic V., "Guidelines, criteria, and rules of thumb for evaluating normed and standardized assessment instruments in psychology," Psychological Assessment, 1994, vol. 6, No. 4, pp. 284-290.
Cox et al., "Evaluation of an in-situ output probe-microphone method for hearing aid fitting verification," Ear and Hearing, Feb. 1990, vol. 11, No. 1, pp. 31-39.
Dirks et al., "Basic acoustic considerations of ear canal: Probe measurements," Ear and Hearing, Oct. 1987, vol. 8, No. 5, pp. 60S-67S.
Feigin et al., "Probe-Tube Microphone Measures of Ear-Canal Sound Pressure Levels in Infants and Children," Ear and Hearing, 1989, vol. 10, No. 4, pp. 254-258.
Gabry et al., "CmdStanR," Interface, Created on Dec. 2023, Retrieved from the Internet: <URL:https://pkgdown.r-lib.org/>, 2 pages.
Gabry et al., "Visualization in Bayesian workflow," Journal of the Royal Statistical Society Series A: Statistics in Society, Feb. 2019, vol. 182, No. 2, pp. 389-402.
Gilman et al., "Acoustics of ear canal measurement of eardrum SPL in simulators," The Journal of the Acoustical Society of America, Sep. 1986, vol. 80, No. 3, pp. 783-793.
Groon et al., "Air-leak effects on ear-canal acoustic absorbance," Ear and Hearing, Jan. 2015, vol. 36, No. 1, pp. 155-163.
Halpin et al., "Effects of universal newborn hearing screening on an early intervention program for children with hearing loss, birth to 3 yr of age," Journal of the American Academy of Audiology, Mar. 2010, vol. 21, No. 3, pp. 169-175.
Holte et al., "Factors Influencing Follow-Up to Newborn Hearing Screening for Infants Who Are Hard of Hearing," American Journal of Audiology, Dec. 2012, vol. 21, pp. 163-174.
Hunter et al., "Multifrequency Tympanometry: Current Clinical Application," American Journal of Audiology. Jul. 1992, vol. 1, No. 3, pp. 33-43.
Hunter et al., "Pediatric Applications of Wideband Acoustic Immittance Measures," Ear and Hearing, Jul. 2013, vol. 34, pp. 36s-42s.
Joint Committee on Infant Hearing, "Year 2019 Position Statement: Principles and Guidelines for Early Hearing Detection and Intervention Programs," Journal of Early Hearing Detection and Intervention, 2019, vol. 4, No. 2, pp. 1-44.
Keefe et al., "Ear-canal impedance and reflection coefficient in human infants and adults," The Journal of the Acoustical Society of America, Nov. 1993, vol. 94, No. 5, pp. 2617-2638.
Keefe et al., "Maturation of the middle and external ears: acoustic power-based responses and reflectance tympanometry," Ear and Hearing. Oct. 1996, vol. 7, No. 5, pp. 361-373.
Kruschke et al., "The Bayesian New Statistics: Hypothesis testing, estimation, meta-analysis, and power analysis from a Bayesian perspective," Psychonomic Bulletin & Review, Feb. 2018, vol. 25, pp. 178-206.
Kruschke, John K., "Doing Bayesian data analysis : a tutorial with R, JAGS, and Stan," 2nd Edition, 2015, Academic Press, 1 page.
Lewis et al., "Comparison of in-situ calibration methods for quantifying input to the middle ear," The Journal of the Acoustical Society of America, Dec. 2009, vol. 126, No. 6, pp. 3114-3124.
Martin et al., "Perforation of the tympanic membrane and its effect on the real-ear-to-coupler difference acoustic transform function," British Journal of Audiology, Aug. 2001, vol. 35, No. 4, pp. 259-264.
Martin et al., "Real ear to coupler differences in children having otitis media with effusion," British Journal of Audiology, Jan. 1996, vol. 30, No. 2, pp. 71-78.
Martin et al., "Real-Ear to Coupler Differences in Children with Grommets," British Journal of Audiology, Feb. 1997, vol. 31, No. 1, pp. 63-69.
Mccreery et al., "Characteristics of Hearing Aid Fittings in Infants and Young Children," Ear and Hearing, Nov. 2013, vol. 34, No. 6, pp. 701-710.
Mccreery et al., "Longitudinal Predictors of Aided Speech Audibility in Infants and Children," Ear and Hearing, Nov. 2015, vol. 36, Supp. 1, pp. 24S-37S.
Mccreery et al., "Predicting children's real-ear-to-coupler differences based on tympanometric data," International Journal of Audiology, May 2023, vol. 62, No. 5, pp. 462-471.
Mccreery et al., "Use of forward pressure level to minimize the influence of acoustic standing waves during probe-microphone hearing-aid verification," The Journal of the Acoustical Society of America, Jul. 2009, vol. 126, No. 1, pp. 15-24.
Merchant et al., "Limited Audiological Assessment Results in Children With Otitis Media With Effusion," Ear and Hearing. Sep. 2023, pp. 1-6.
Miller et al., "Pure-tone audiometry with forward pressure level calibration leads to clinically-relevant improvements in test-retest reliability," Ear and Hearing. Sep. 2018 vol. 39, No. 5, pp. 946-957.
Moeller et al., "An Introduction to the Outcomes of Children with Hearing Loss Study," Ear and Hearing, Nov. 2015, vol. 36, pp. 4S-13S.

(56) References Cited

OTHER PUBLICATIONS

Moeller, Mary Pat, "Early Intervention and Language Development in Children Who Are Deaf and Hard of Hearing," Pediatrics., Sep. 2000, vol. 106, No. 3, pp. 1-9.
Moodie et al., "Pediatric audiology in North America: Current clinical practice and how it relates to the American Academy of Audiology pediatric amplification guideline," Journal of the American Academy of Audiology, Mar. 2016, vol. 27, No. 3, pp. 166-187.
Moodie et al., "Procedure for Predicting Real-Ear Hearing Aid Performance in Young Children," American Journal of Audiology, Mar. 1994, vol. 3, No. 1, pp. 23-31.
Mueller, H. G., "Probe Microphone Measurements: 20 Years of Progress," Trends in Amplification, Jun. 2001, vol. 5, No. 2, pp. 35-68.
Munro et al., "Comparison of Real-Ear to Coupler Difference Values in the Right and Left Ear of Adults Using Three Earmold Configurations," Ear and Hearing, Jun. 2005, vol. 26, No. 3, pp. 290-298.
Munro et al., "Customized acoustic transform functions and their accuracy at predicting real-ear hearing aid performance," Ear and Hearing, Feb. 2000, vol. 21, No. 1, pp. 59-69.
Neely et al., "Forward-pressure level for in-the-ear calibration," Journal of the Acoustical Society of America, Mar. 2010, vol. 127, No. 3, pp. 1-27.
Oleson et al., "The Evolution of Statistical Methods in Speech, Language, and Hearing Sciences," Journal of Speech, Language, and Hearing Research, Mar. 2019, vol. 62, No. 3, pp. 498-506.
Scheperle et al., "Influence of in situ, sound-level calibration on distortion-product otoacoustic emission variability," The Journal of the Acoustical Society of America, Jul. 2008, vol. 124, No. 1, pp. 288-300.
Shanks et al., "Basic principles and clinical applications of tympanometry," Clinics Audiology, Apr. 1991, vol. 24, No. 2, pp. 299-328.
Siegel, J. H., "Ear-canal standing waves and high-frequency sound calibration using otoacoustic emission probes," Journal of the Acoustical Society of America, May 1994, vol. 95, No. 5, pp. 2589-2597.
Tomblin et al., "Aided Hearing Moderates the Academic Outcomes of Children With Mild to Severe Hearing Loss," Ear and Hearing, Jul. 2020, vol. 41, No. 4, pp. 775-789.
Tomblin et al., "Language Outcomes in Young Children with Mild to Severe Hearing Loss," Ear and Hearing, Nov. 2015, vol. 36, pp. 76S-91S.
Tomblin et al., "The Influence of Hearing Aids on the Speech and Language Development of Children With Hearing Loss," JAMA Otolaryngology—Head & Neck Surgery, May 2014, vol. 140, No. 5, pp. 403-409.
Vaisberg et al., "Evaluation of the Repeatability and Accuracy of the Wideband Real-Ear-to-Coupler Difference," Journal of the American Academy of Audiology, Jun. 2018, vol. 29, pp. 520-532.
Van Eeckhoutte et al., "Perceptual Benefits of Extended Bandwidth Hearing Aids With Children: A Within-Subject Design Using Clinically Available Hearing Aids," Journal of Speech, Language, and Hearing Research, Nov. 2020, vol. 63, No. 11, pp. 3834-3846.
Van Eeckhoutte et al., "Speech recognition, loudness, and preference with extended bandwidth hearing aids for adult hearing aid users," International Journal of Audiology, Oct. 2020, vol. 59, No. 10, pp. 780-791.
Vehtari et al., "Erratum to: Practical Bayesian model evaluation using leave-one-out cross-validation and WAIC," Statistics and Computing, 2017, vol. 27, 1 page.
Voss et al., "Acoustic mechanisms that determine the ear-canal sound pressures generated by earphones," The Journal of the Acoustical Society of America, Mar. 2000, vol. 107, No. 3, pp. 1548-1565.
Voss et al., "How does the sound pressure generated by circumaural, supra-aural, and insert earphones differ for adult and infant ears?" Ear and Hearing, Dec. 2005, vol. 26, No. 6, pp. 636-650.
Voss et al., "Middle ear pathology can affect the ear-canal sound pressure generated by audiologic earphones," Ear and Hearing, Aug. 2000, vol. 21, No. 4, pp. 265-274.
Watts et al., "Relationship of Head Circumference and Age in the Prediction of the Real-Ear-to-Coupler Difference (RECD)," Journal of the American Academy of Audiology, Jul. 2020, vol. 31, pp. 496-505.
Wood et al., "Performance and characteristics of the Newborn Hearing Screening Programme in England: The first seven years," International Journal of Audiology, Jun. 2015, vol. 54, No. 6, pp. 353-358.
Zwislocki, J., "Analysis of the Middle-Ear Function. Part I: Input Impedance," The journal of the Acoustical Society of America, Sep. 1962, vol. 34, No. 8, pp. 1514-1523.
Bagatto et al., "Real-Ear-to-Coupler Difference Predictions as a Function of Age for Two Coupling Procedures," J Am Acad Audiol, 2002, vol. 13, pp. 407-415.
International Search Report and Written Opinion in PCT/US2023/072212, mailed Dec. 8, 2023, 13 pages.
Liu et al., "Wideband absorbance tympanometry using pressure sweeps: System development and results on adults with normal hearing," J. Acoust. Soc. Am., 2008, vol. 124, No. 6, pp. 3708-3719.

* cited by examiner

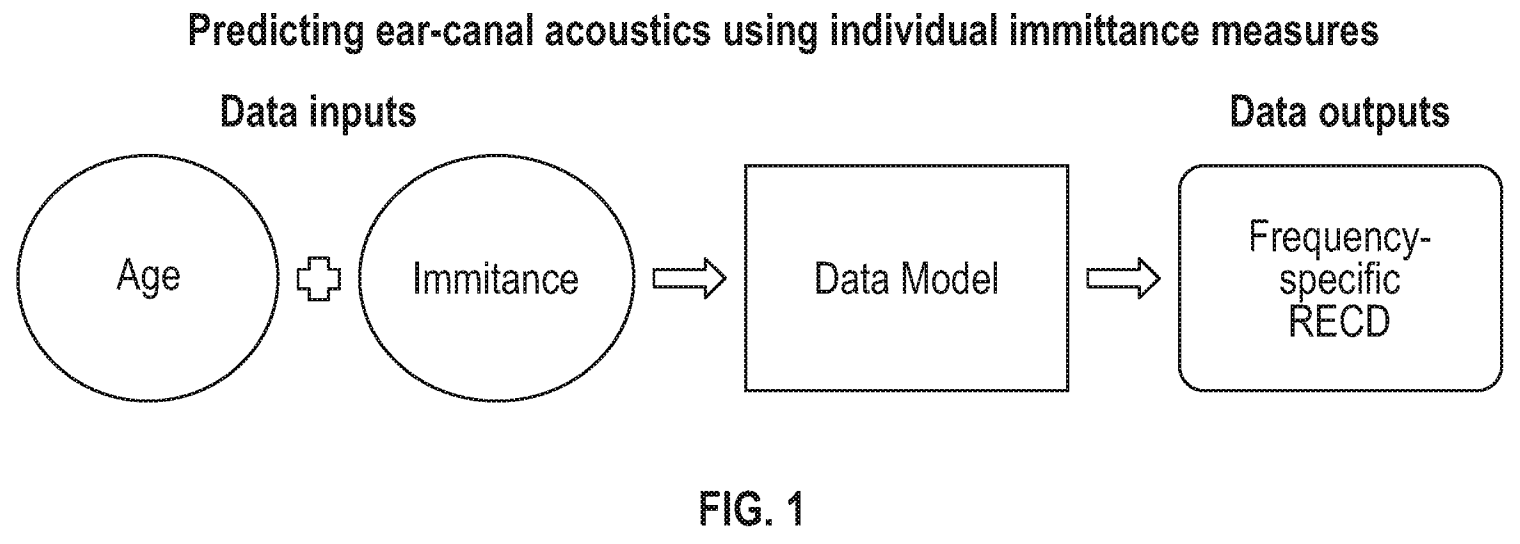

Predicting ear-canal acoustics using individual immittance measures

Data inputs

Age

Immitance

Data Model

Data outputs

Frequency-specific RECD

FIG. 1

PREDICTING REAL-EAR-TO-COUPLER DIFFERENCES BASED ON CLINICAL IMMITTANCE MEASURES OF THE MIDDLE EAR

CROSS REFERENCE TO RELATED APPLICATIONS

This application claims priority under 35 U.S.C. § 119 to provisional patent application U.S. Ser. No. 63/371,441, filed Aug. 15, 2022. The provisional patent application is herein incorporated by reference in its entirety, including without limitation, the specification, claims, and abstract, as well as any figures, tables, appendices, or drawings thereof.

FIELD OF THE INVENTION

The invention relates generally to systems, apparatus, and/or corresponding methods in at least the audiometry industry. More particularly, but not exclusively, the invention relates to systems, methods, and/or apparatus for improved predictions for real-ear-to-coupler differences to improve estimates of hearing thresholds and hearing-aid output in the ear canal based on clinical immittance measures of the middle ear, which improve on currently used, age-based estimates when the real-ear-to-coupler difference cannot be directly measured.

BACKGROUND OF THE INVENTION

Over the last two decades, the average age of identification of hearing loss has been reduced from over 2-years of age to under 6-months, allowing a greater number of children with hearing loss to receive hearing aids and intervention within the first few months of life. This rapid progress necessitated the development of objective hearing-aid verification methods to ensure that speech is audible and that the sound levels produced by the hearing aids are safe. Direct measurement of the hearing-aid output in the ear canal with a probe microphone, known as real-ear or in situ verification, is the gold-standard approach for measuring hearing-aid output. In situ verification can be difficult to complete with infants and young children because it requires head control, cooperation from the child, and multiple measurements in each ear. As an alternative to in situ hearing-aid verification, a single measurement of the child's ear canal acoustics, known as the real-ear-to-coupler difference (RECD), can be applied to hearing-aid measurements in a coupler to accurately simulate the output of the hearing aid in the child's ear canal. Despite requiring only a single measurement, however, the RECD still may be difficult to measure due to limited cooperation or middle ear problems. Age-based normative RECD values are available as a reasonable approximation of a child's ear canal acoustics, but individual variability in ear-canal size and length among children means that the child's actual RECD can differ from average by as much as +/−10 dB at any given age and frequency. This inaccuracy can compromise aided audibility for speech and other important sounds through the hearing aid or lead to over-amplification.

Therefore, there is a need in the art to apply supplemental outer and middle ear-canal acoustics data from standard clinical immittance measures to improve predictions of the RECD when it cannot be easily measured.

The primary goal of fitting hearing aids for children with hearing loss is to ensure access to the acoustic cues that are needed to promote speech and language development as soon after the diagnosis of hearing loss as possible. Quantifying speech audibility through a hearing aid for infants and young children is challenging because individual variability in ear canal acoustics can have a substantial influence on the output characteristics of hearing aids, even among children who are the same age. Studies examining the variability in hearing-aid output for different makes of hearing aids found that manufacturer default gain settings vary by as much as 20 dB among adults due in part to individual differences ear-canal acoustics and variation in the amount of occlusion of the ear canal from the hearing aid or earmold. For infants and young children, variability in ear canal acoustics is dynamic over time due to changes in ear canal volume, length, and mechanical properties (e.g., ear canal wall compliance). Growth leads to variability in hearing aid output as children get older. Hearing-aid verification measurements using probe microphones were developed to help characterize these sources of variability across individuals and over time. A flexible, probe microphone tube is placed in the ear canal, the hearing aid is inserted, and the probe-microphone system measures the output of the hearing aid in the ear canal in reference to a sound presented via a loudspeaker in front of the listener. The output of the hearing aid is compared to hearing thresholds converted to dB SPL to estimate the audibility of the amplified speech signal and compare the output to prescriptive targets.

For infants and young children, the need to quantify the output of the hearing aids in the ear canal is paramount to ensuring audibility for speech and to prevent hearing damage from over-amplification, but in situ probe-microphone measures are often not possible due to child cooperation or other factors. As an alternative to in situ probe-microphone verification, the RECD is a single measurement of a child's ear-canal acoustics that can be applied to hearing-aid measurements in a coupler. A measurement of broadband noise is taken in the coupler used for hearing aid verification in a test box. The same signal is delivered to the child's occluded ear canal via their hearing-aid earmold or an insert earphone foam tip. The difference in dB between the measurement in the child's ear canal and the coupler is the RECD. The RECD is applied to hearing-aid measurements in a coupler to simulate the in situ hearing-aid output. Smaller ear canals produce larger RECD values, and the RECD decreases as children's ear canals grow and approximate adult size and length. The use of the RECD for simulated hearing-aid verification has been validated in multiple studies involving thousands of children and more recently has been adapted to improve accuracy at high frequencies as the wideband RECD (wRECD).

Even though the RECD is a practical and widely used alternative when in situ hearing-aid verification cannot be completed, there are still barriers to measuring individual RECD. Fitting hearing aids without estimates of ear-canal acoustics could compromise speech audibility and safety of hearing aid fittings of infants and young children. A survey of hearing-aid verification practices for pediatric audiologists found that just under half of audiologists used in situ hearing-aid verification often or always with young children, and only around 60% of audiologists reported measuring each child's individual RECD at the time of hearing aid verification. The most common reason reported in the survey for not measuring in situ verification or RECD was lack of cooperation from the child during probe-microphone measurements. An earlier study of children fitted with hearing aids found that audiologists used an age based average RECD instead of the child's individually measured RECD in over 40% of fittings and that fittings based on average RECD had greater deviations from prescriptive targets than fittings where the RECD was individually measured. The reduced accuracy for hearing-aid verification when an average RECD is used is not surprising, as average RECD data has a 10-15 dB range at each age for normal ear canals. These studies demonstrate that although the RECD is a valuable tool for pediatric hearing aid verification, there are barriers, including child cooperation, which can limit its use.

One major contributing factor to individual differences in RECD among children and over time is the variation in acoustic impedance of the ear canal across listeners. Differences in ear-canal volume and outer- and middle-ear impedance influence the sound pressure level measured in the occluded ear canal. Acoustic models have demonstrated that variation in ear-canal sound pressure levels is associated with differences in impedance related to larger residual ear-canal volume that occurs with circumaural headphones compared to insert earphones. Higher impedance resulting from smaller residual ear-canal volume led to higher sound pressure levels than the lower impedance coupling from circumaural headphones with differences as large as 35 dB across earphone types for the same listener. These studies demonstrated the potential impact of individual differences in impedance on variability in audiometric assessment across earphones but did not directly assess how these differences in impedance would influence individual RECD values in the context of hearing aid verification.

Few studies have directly assessed the potential to predict individual differences in RECD based on individual impedance characteristics. Impedance differences across individual ear canals measured with insert earphones are consistent with differences in ear-canal sound pressure levels observed in studies of age-related changes in the RECD as the ear canal grows and adult-child differences in pressure levels between circumaural and insert earphones. Consistent with previous work, the RECD is larger in ears with middle-ear effusion where impedance is higher, but smaller at low frequencies in ears with pressure equalization tubes or tympanic membrane perforations when impedance is reduced by the increased volume of the middle-ear cavity.

In contrast, individual measures of the impedance of the ear canal and middle ear often are readily available in young children from measures of acoustic immittance, such as tympanometry. Acoustic immittance measures are already routinely conducted in children with hearing loss. Tympanometry is a pressurized measure of middle-ear function that uses a probe tone to estimate the amount of sound that is absorbed by the middle ear. The most common approach to tympanometry uses a 226 Hz probe tone to assess the function of the middle ear at low frequencies and has reasonable sensitivity for detecting the presence of fluid in the middle-ear space. Wideband acoustic immittance (WAI) is a different clinical immittance measure that uses a broadband stimulus, such as a click, to assess absorbance across a broader range of frequencies than single-frequency tympanometry. Tympanometry and WAI provide an estimate of the equivalent volume of the ear canal which has a direct impact on the impedance of the occluded ear canal. Tympanometry and WAI are performed in infants and young children as part of clinical audiology visits and is typically available for children with hearing loss as part of a standard clinical audiology visit, even if the RECD cannot be individually measured. However, it is unclear whether differences in immittance characteristics from tympanometry or WAI could be useful in improving predictions of individual differences in ear-canal acoustics as measured by the RECD above using the age-based average RECD values alone. Average RECD data are available for children with normal middle-ear function, but normative data for children who have middle ear fluid, perforations, and tympanostomy tubes have not been published. The lack of normative data for children with middle-ear dysfunction is a major problem that can lead to errors in hearing-aid fitting, as these middle ear conditions among the most frequently occurring health conditions for infants and young children and are known to affect the RECD.

In recent years, advances in computing and statistical techniques have led to the potential to apply alternative analytic methods that do not require the same rigid assumptions as frequentist approaches based on null-hypothesis % significance testing. Frequentist statistical approaches assume that a model must be tested against the probability that the effects of the model would be observed by chance. These modelling approaches produce estimates and distributions of effects that assess the magnitude and certainty of parameters that could be used to predict RECD when it cannot be measured with greater accuracy than age-based estimates.

Thus, there exists a need in the art for systems, methods, and/or apparatus to determine if individual differences in static admittance and ear-canal volume derived from 226 Hz tympanometry and/or WAI could be used to predict individual differences in measured RECD for children.

SUMMARY OF THE INVENTION

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the invention to improve on or overcome the deficiencies in the art.

It is another object, feature, and/or advantage to apply supplemental outer and middle ear-canal acoustics data from standard clinical immittance measures, including 226 Hz tympanometry and WAI, to improve predictions of the RECD when it cannot be easily measured.

It is a further object, feature, and/or advantage to determine if individual differences in immittance characteristics, specifically static admittance and ear-canal volume derived from 226 Hz tympanometry and/or wideband acoustic immittance measurements, could be used to predict individual differences in measured RECD for children.

It is still yet a further object, feature, and/or advantage to provide clinical data to improve the predicted results over standard, age-based data.

It is yet another object, feature, and/or advantage to provide clinical tools, including diagnostic tools, which include both age-based data and collected tympanometric and/or immittance data to improve upon predicted calculations related to measured RECD for children with normal and abnormal middle ear functions.

The systems, methods, and/or clinical apparatus disclosed herein can be used in a wide variety of applications. For example, the aspects and/or embodiments disclosed can be used in clinical settings to provide improved estimates for ear conditions, such as hearing aid testing.

It is preferred the apparatus be safe, cost effective, and durable.

At least one embodiment disclosed herein comprises a distinct aesthetic appearance. Ornamental aspects included in such an embodiment can help capture a consumer's attention and/or identify a source of origin of a product being sold. Said ornamental aspects will not impede functionality of the invention.

Methods can be practiced which facilitate use, manufacture, assembly, maintenance, and repair of a clinical apparatus which accomplish some or all of the previously stated objectives.

The methods and/or systems disclosed can be incorporated into systems or kits which accomplish some or all of the previously stated objectives. This includes diagnostic tools, clinical tools, and other testing apparatus.

According to some aspects of the present disclosure, [first independent claim 1].

According to some additional aspects of the present disclosure, [dependent claims].

According to some other aspects of the present disclosure, [subsequent independent claim].

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

Several embodiments in which the invention can be practiced are illustrated and described in detail, wherein like reference characters represent like components throughout the several views. The drawings are presented for exemplary purposes and may not be to scale unless otherwise indicated.

FIG. 1 is a flow diagram of inputs and outputs of a data model according to aspects and/or embodiments of the present disclosure.

Figure 2:
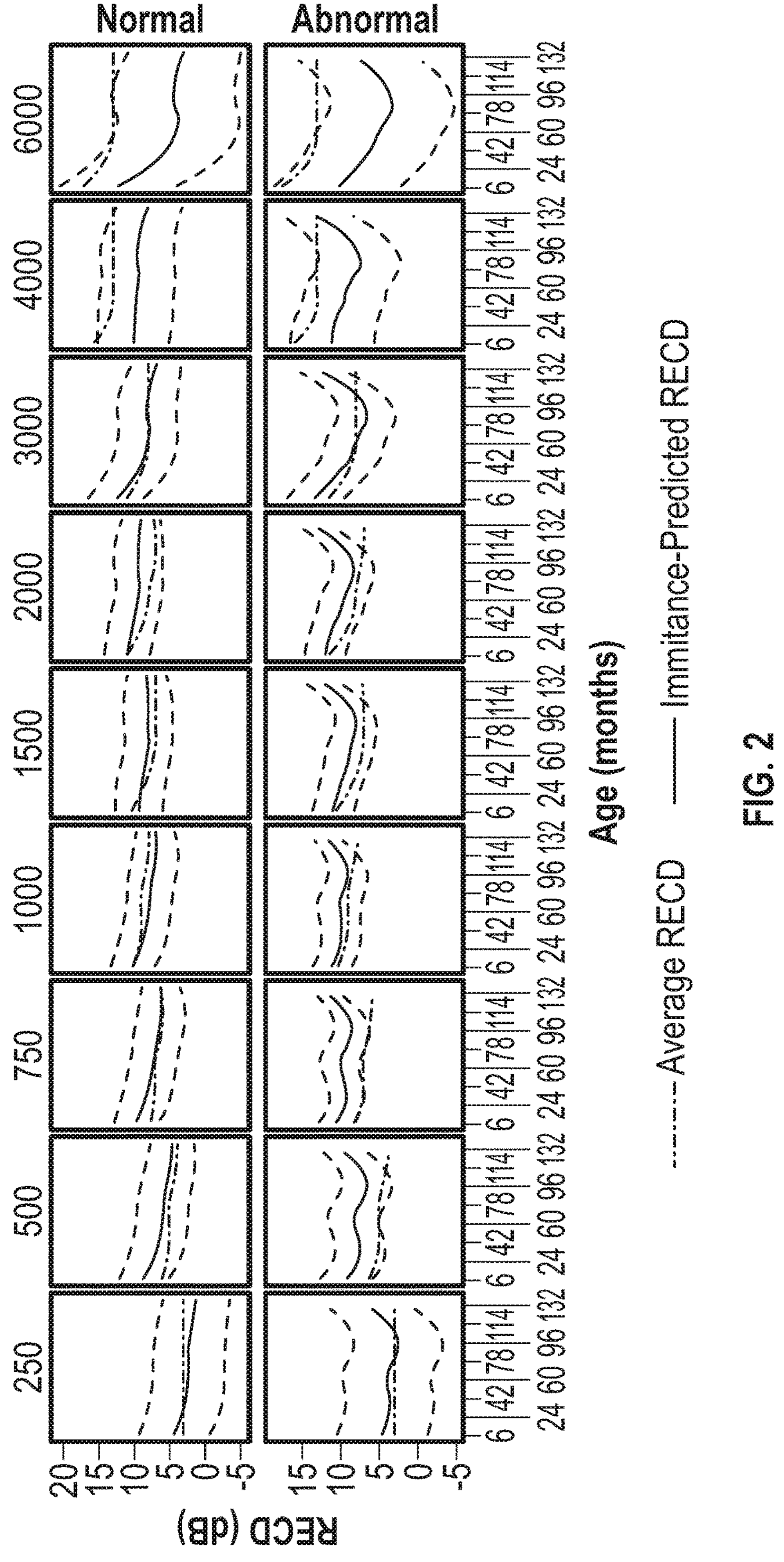
FIG. 2 is a graph showing model-predicted real-ear-to-coupler differences (black solid line) and measured real-ear-to-coupler differences by age and frequency. Dashed black lines represent the 89% credible interval for the model predictions.

An artisan of ordinary skill need not view, within isolated figure(s), the near infinite number of distinct permutations of features described in the following detailed description to facilitate an understanding of the invention.

DETAILED DESCRIPTION OF THE INVENTION

The present disclosure is not to be limited to that described herein. Mechanical, electrical, chemical, procedural, and/or other changes can be made without departing from the spirit and scope of the invention. No features shown or described are essential to permit basic operation of the invention unless otherwise indicated.

Unless defined otherwise, all technical and scientific terms used above have the same meaning as commonly understood by one of ordinary skill in the art to which embodiments of the invention pertain.

The terms "a," "an," and "the" include both singular and plural referents.

The term "or" is synonymous with "and/or" and means any one member or combination of members of a particular list.

The terms "invention" or "present invention" are not intended to refer to any single embodiment of the particular invention but encompass all possible embodiments as described in the specification and the claims.

The term "about" as used herein refer to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of said quantifiable variable, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

The term "real-ear-to-coupler difference" (RECD) means the occluded response of the ear canal.

The term "wideband acoustic immittance" (WAI) refers to a group of acoustic measurements that provide detailed mechanical and acoustic information (i.e., absorbance, power reflectance, admittance, and impedance, among others). WAI measurements are made in the ear canal in response to wideband stimuli (e.g., a click or chirp) and compare a sound input to the absorbed or reflected portions of that sound.

The term "static admittance" refers to the maximum compliance (mobility) of the middle ear system (i.e., the greatest amount of acoustic energy absorbed by the middle ear system (the vertical peak of the tympanogram tracing).

The term "absorbance" refers to a measure of the effectiveness of the middle ear (to absorb sound) as a function of frequency.

The term "hearing aid" or "hearing aid device" refers to a device designed to improve hearing by making sound audible to a person with hearing loss. Such hearing aid includes, but is not limited to, body-worn devices, behind the ear devices, in the ear devices, invisible-in-canal hearing aids, extended wear hearing aids, CROS hearing aids, eyeglass aids, osseointegrated auditory prosthesis (formerly called the bone-anchored hearing aid), cochlear implants. stethoscopes, and hearing aid applications.

The "scope" of the invention is defined by the appended claims, along with the full scope of equivalents to which such claims are entitled. The scope of the invention is further qualified as including any possible modification to any of the aspects and/or embodiments disclosed herein which would result in other embodiments, combinations, subcombinations, or the like that would be obvious to those skilled in the art.

As will be understood, aspects and/or embodiments disclosed herein include the use of frequentist models to test the null hypothesis that the effect of including immittance data along with an average RECD is different than a model predicting a person's measured RECD based on the average RECD alone. According to at least some aspects and/or embodiments, the person is a child. However, while reference to children may be used throughout the present disclosure, it should be appreciated that this is for example purposes, and it is not to be limiting on the disclosure. In other words, while the disclosure may include reference to children, including known information for certain age of children (e.g., RECD data based on age), it is to be appreciated that the systems, methods, and/or apparatus disclosed herein may be utilized and configured to be used for people of all ages.

A Bayesian statistical framework is ideal for providing estimates of the probability and magnitude of errors introduced by different models. Frequentist models do not consider prior knowledge about the relationships between variables to avoid bias in the model. In the case of RECD, there is an extensive literature on the RECD and outer and middle ear acoustics that suggests that using a null hypothesis to address the research questions addressed herein would provide predictable results and generally be uninformative for clinicians. Additionally, because a goal of the present disclosure was to quantify the relationships between individuals' middle-ear acoustics and RECD values, the distributions of parameter values (e.g., regression coefficients) that result from Bayesian statistical models are ideal for evaluating not only the probability of parameter estimates and potential errors that could result from using an average RECD alone compared to the average RECD with immittance data but also quantification of uncertainty. Bayesian approaches calculate parameter probabilities directly from observed data. Bayesian analyses do not require calculation of p values or their associated confidence intervals, as with frequentist approaches. Rather, uncertainty is quantified directly from the calculated distributions of parameters. This approach can be useful for applying the results of the model to clinical decisions about the range and likelihood of potential errors that could result from the two alternative approaches.

As will be understood, a goal addressed by the present disclosure includes a determination if individual differences in static admittance and ear-canal volume derived from 226 Hz tympanometry could be used to predict individual differences in measured RECD for children. It was hypothesized that children with larger ear-canal volumes and greater admittance would be associated with smaller RECD values due to changes in impedance with ear canal size. It was also hypothesized that the model including immittance information would provide more accurate estimates of the child's measured RECD than an average RECD based on the child's age. The difference between the average RECD and the child's measured RECD was used to assess whether immittance measures could be applied in combination with an age-based average RECD to develop a more accurate approximation of each child's measured RECD for clinical situations where the RECD cannot be measured. Comparisons between average RECD models and models that used average RECD and immittance were also compared for children with tympanostomy tubes or tympanic membrane perforations to determine if these models could provide normative values and predictions of RECD for children with those conditions where using average RECD could lead to hearing aid fitting errors.

The information obtained from the models can be used in a number of ways. For example, the information could be used to determine the effectiveness or provide an estimate for the use of hearing aid devices (e.g., in ear hearing aids) in a non-invasive manner. It will be understood that the models can be used to train a machine learning network to be used in a clinical setting, such as via a non-invasive clinical apparatus (e.g., an acoustic measuring apparatus) to provide contemporaneous results to estimate the effectiveness of hearing aid devices in a non-invasive manner, and with improved results when compared to standard, age-based averages alone.

To develop and test the models described herein, the following materials and methods were utilized. It is to be appreciated that the following are provided for examples and background information, and are not to be limiting on the disclosure itself.

Participants: Two-hundred sixty-six children with permanent hearing loss provided data for the analysis disclosed herein. Children were recruited from 16 states in the U.S. as part of the multicenter Outcomes of Children with Hearing Loss study. The children ranged in age from 7 months to 12 years. Inclusion criteria for the study were that English had to be the primary language spoken in the home, and the child could not have additional disabilities that were diagnosed at the time of enrollment in the study. For children who received cochlear implants, only data from visits prior to cochlear implantation are included in these analyses. The mean better-ear pure tone average at 500, 1000, and 2000 Hz for the group was 48.5 dB HL. The number of visits with RECD data by the child's sex and age group are shown in Table 1. The procedures were approved by the IRB Boards of the participating institutions.

TABLE 1

Number of study visits with RECD by Child's sex and age group

| | Child's Sex | | Number of Visits with RECD | | | | |
|---|---|---|---|---|---|---|---|
| Age | Female | Male | 1 | 2 | 3 | 4 | 5 or more |
| 1 year or less | 16 | 28 | 15 | 18 | 4 | | |
| 2 years | 33 | 37 | 36 | 15 | 12 | 7 | |
| 3 years | 52 | 47 | 31 | 27 | 21 | 15 | 5 |
| 4 years | 55 | 66 | 42 | 42 | 22 | 12 | 2 |
| 5 years | 80 | 68 | 44 | 41 | 41 | 17 | 5 |
| 6-9 years | 232 | 231 | 41 | 117 | 55 | 81 | 56 |
| 10-12 years | 84 | 105 | | 2 | | 84 | 16 |

Materials: Tympanometry was measured using either a Grason-Stadler TympStar (Eden Prairie, MN) or Welch Allyn Audioscope 2 (Skaneateles Falls, NY). Audioscan Verifit 1 or RM 500SL probe microphone systems (Dorchester, ON) were used to measure individual RECDs. However, any device capable of acquiring/obtaining the acoustic measurements from an ear canal are to be considered equivalents and are part of the present disclosure.

Procedure: All testing took place in a sound-treated audiometric test booth or mobile test van by a pediatric audiologist. Tympanometry was conducted in conjunction with audiometric examination. Individual RECDs were measured as part of the hearing-aid verification process for the study whenever in situ verification was not possible. The child was seated approximately 2-feet from the verification system, and a probe microphone was placed in the ear canal approximately 10-mm past the end of the earmold sound bore. A transducer was connected to the tubing of each child's earmold. The earmold was inserted over the probe microphone and sound was delivered to the ear canal via the transducer. The transducer delivered a 60 dB SPL broadband noise signal to the child's ear for 10 seconds or until the acoustic response stabilized. The process was repeated for the opposite ear. The same measurement of broadband noise at 60 dB SPL was completed in the 2 $cm^3$ coupler that was used for hearing aid verification. The difference between the coupler response and the response measured in the child's ear canal was the RECD. The frequency-specific average RECD data for each child were derived based on the child's age at the time of the study. Average data were in 1-month intervals for children under 5-years of age and 1-year intervals for children over 5-years of age.

Statistical Analysis: The analyses were conducted under a Bayesian framework to estimate directly the most probable set of parameter values, including distributional parameters, which explain the data as well as quantifying the uncertainty surrounding parameter estimates. All models were constructed using the Stan programming language through the rstan and brms packages in R statistical computing software.

Regression models commonly only model the location parameter as dependent on predictors while other distributional parameters (scale and shape parameters, for example) are not modelled directly and are often assumed to be constant. Because the shape and position of RECD data distributions are known to differ by frequency and middle-ear status, the data was modelled as a Student's t distribution:

$$f(y) = \frac{\Gamma((\nu+1)/2)}{\Gamma(\nu/2)} \frac{1}{\sqrt{\nu\pi}\,\sigma}\left(1 + \frac{1}{\nu}\left(\frac{y-\mu}{\sigma}\right)^2\right)^{-(\nu+1)/2}$$

where $\Gamma$ denotes the gamma function and $\nu>1$ are the degrees of freedom (note that as $\nu \Rightarrow \infty$, the Student's t distribution becomes the normal distribution) and estimated $\sigma$ and $\nu$ directly.

Pearson's correlations quantify linear relationships between two normally distributed variables. The normal distribution and its multivariate generalization, the multivariate normal distribution, are sensitive to outliers. Use of the Student's t distribution for regression is particularly advantageous for data with outliers; when $\nu$ is small, the Student's t distribution is more robust to multivariate outliers. When outliers are present in the data, those cases may be overly influential resulting in distortion of correlation estimates. The Student's t distribution can produce better correlation estimates when outliers are present in the data.

To address the research questions about the potential benefits of incorporating individual measures of ear-canal acoustics from clinical tympanometry to enhance predictions of the child's RECD, the model was constructed of measured RECDs; with population-level effects of average RECD, frequency, middle-ear status (normal [admittance $\geq$0.3 mL, tympanometric peak pressure >−150 daPa, and ear-canal volume 0.4-2.0 $cm^3$] vs. abnormal [any value outside boundaries of normal), ear-canal volume (ECV), 226 Hz tympanometric peak pressure, 226 Hz admittance, and interaction terms for average RECD×frequency and middle-ear status×frequency. Continuous predictor variables were standardized by subtracting the variable mean and then dividing by its standard deviation.

Varying effects of frequency and middle-ear status were included, as well as group-level effects of subjects' individual ears and year of measurement. The distributional effects of variance ($\sigma$) r and degrees of freedom ($\nu$) were estimated with varying effects of frequency grouped by middle-ear status.

The immittance model, including the aspects and/or embodiments disclosed herein, was evaluated and compared with a Gaussian/Normal model with only average RECD, frequency, and their interaction as population-level effects using Pareto smoothed importance sampling leave-one-out cross-validation (PSIS-LOO). PSIS-LOO is a way of estimating pointwise out-of-sample predictive accuracy of a fitted Bayesian model. PSIS-LOO estimates the expected log predictive density (ELPD), which can be used to evaluate and compare different models relative to observed data. High generalized Pareto distribution shape parameters (k>0.7) often result from model misspecification and data points considered outliers. The evaluation of the disclosed model indicates good reliability and convergence rates of the PSIS-based estimates with 99.9% of estimated Pareto k values below 0.7. A difference in PSIS-LOO ELPD of 3-5 times greater than the standard error (SE) is considered a significant improvement. Comparing the models, the immittance model according to aspects and/or embodiments disclosed herein has shown a significantly better fit to the data relative to the average RECD and Frequency only Gaussian model with a difference in ELPD of 2436.0 (SE of 83.3) in favor of the immittance model.

Accordingly, one aspect of the immittance model is shown in FIG. 1, which is a flow diagram showing the inputs used and outputs from the model that would be generated. This model may be referred to as acoustic measurement models. In such a model, the two main inputs are the child's age in months and data from clinical immittance measures. The immittance inputs could be based on either 226 Hz tympanometry or wideband acoustic immittance. For 226 Hz tympanometry, the inputs would be the equivalent ear-canal volume ($cm^3$), static admittance (mmhos), and tympanometric peak pressure (daPa). For wideband immittance, the inputs would include the same estimates of equivalent ear-canal volume and tympanometric peak pressure, but would include frequency-specific absorbance in one-third octave bands from 200 Hz-10,000 Hz. These inputs are applied to the data model to derive frequency-specific RECD values (in dB) for one-third octave bands over the same frequency ranges as the inputs. The data model has two separate branches for intact vs. non-intact tympanic membrane. The output for the data model would be resemble age specific values by frequency shown as the solid black line in FIG. 2, which includes model-predicted real-ear-to-coupler differences (black solid line) and measured real-ear-to-coupler differences by age and frequency. Dashed black lines represent the 89% credible interval for the model predictions.

Figure 3:
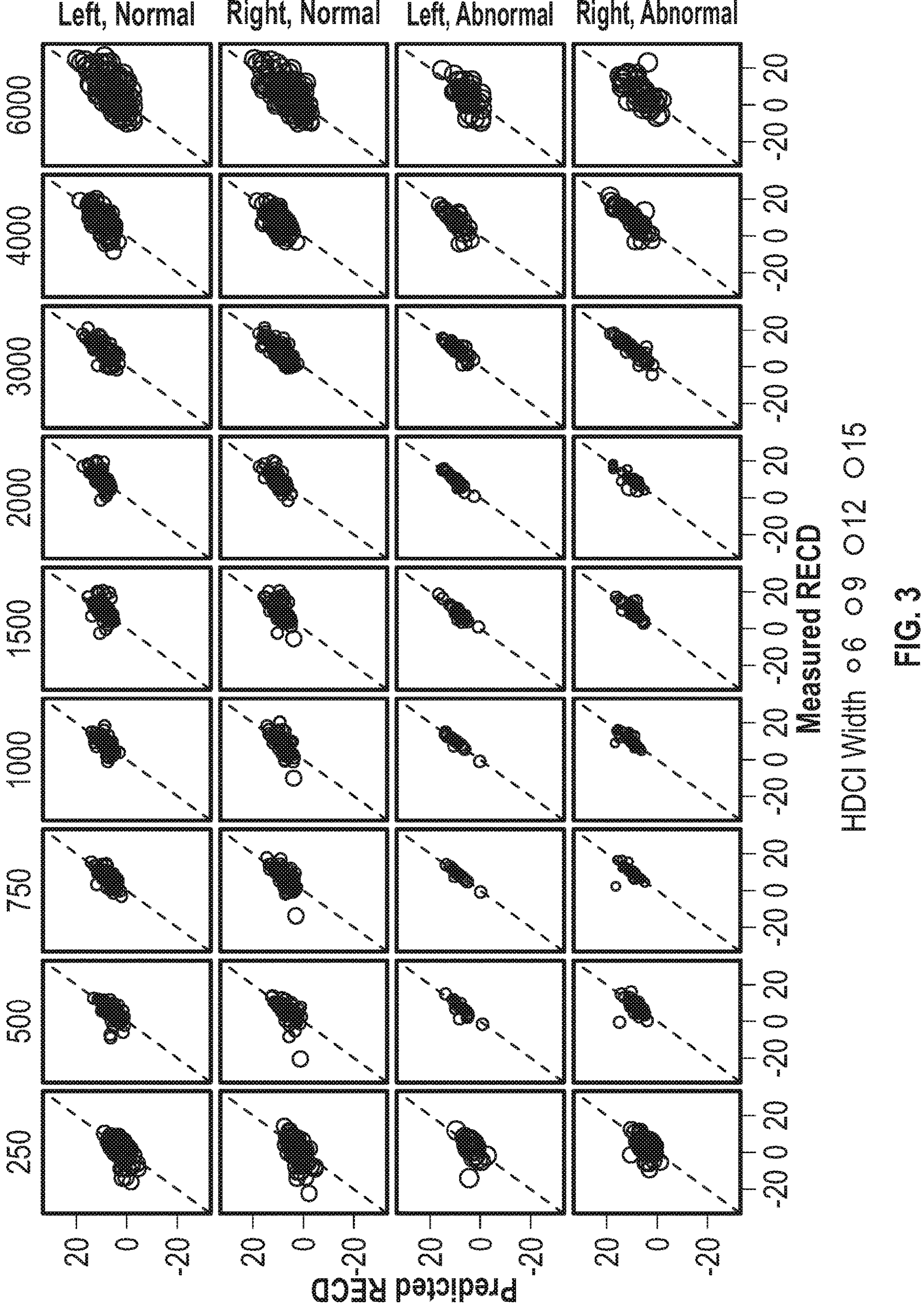
FIG. 3 is a graph showing an immittance model predicted real-ear-to-coupler (RECD) plotted by measured RECD with rows of panels for ear (left vs. right) and middle ear status (normal vs. abnormal) and columns for each frequency in hertz.

FIG. 3 depicts immittance model predicted RECDs versus measured RECDs by frequency, ear, and middle-ear status. In general, the model predictions of RECD were concentrated along the diagonal for frequencies from 500 Hz-4000 Hz. Greater uncertainty of model estimates was observed at 250 Hz and 6000 Hz as evidenced by larger symbols off the diagonal line. As there were no significant differences between ears for each subject for the immittance model and the average RECD model would use the same RECD for both left and right ears, further visualization of comparisons between immittance and average RECD models are collapsed across ears to simply these comparisons.

Figure 4:
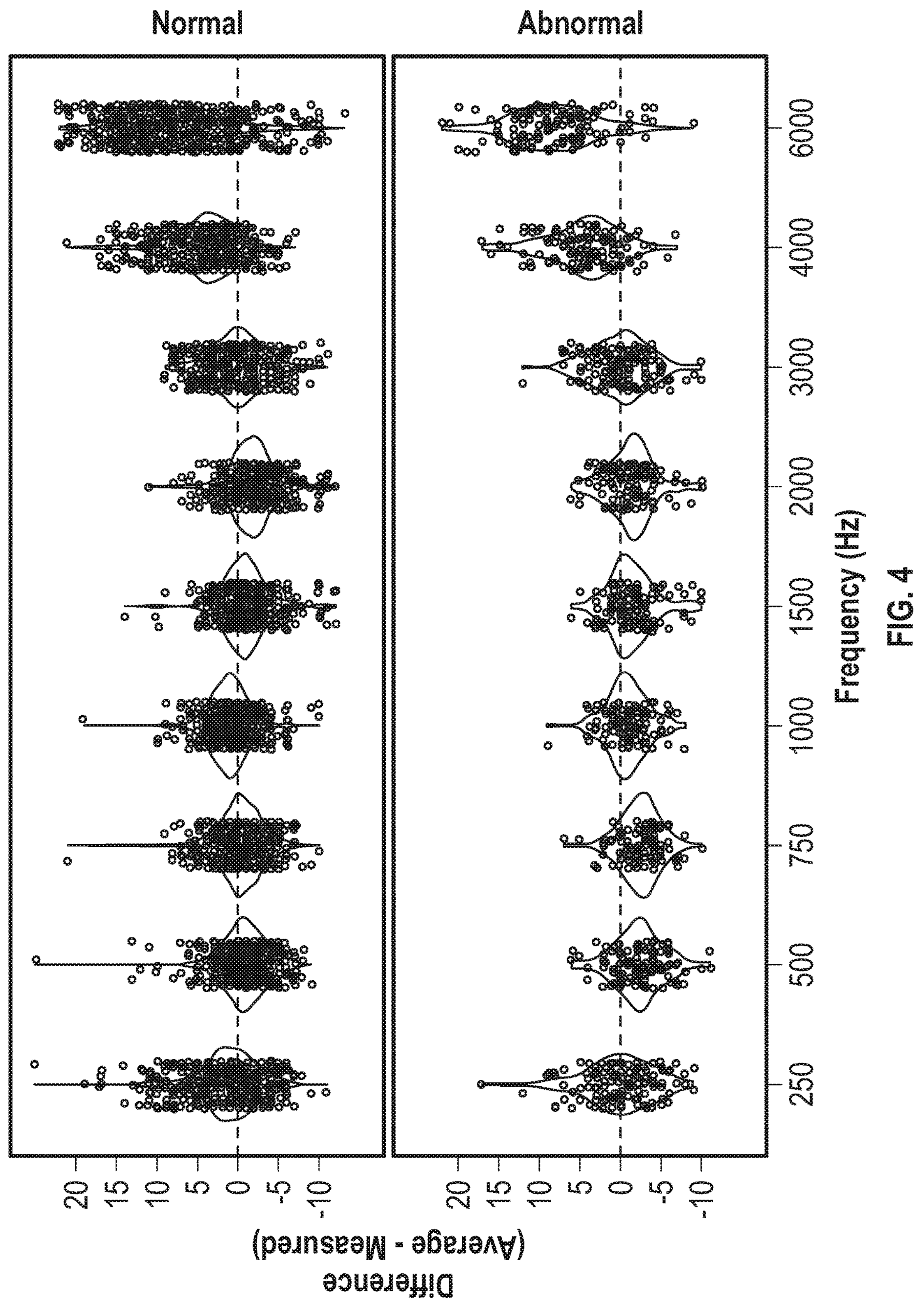
FIG. 4 is a graph showing violin plots of the differences between average and measured RECD in dB plotted by frequency for normal middle ear status (top panel) and abnormal middle ear status (bottom panel).

FIG. 4 shows the difference between average RECD and measured RECD for the participants in the study to represent the magnitude of estimation errors that would be made using an average RECD instead of measured RECD for this sample. For 500 Hz-3000 Hz, the distribution of differences between average RECD and measured RECD was centered around 0 dB with a range of +20 dB to −10 dB for children with normal and abnormal middle ear status. At 250 Hz, 4000 Hz and 6000 Hz, the average RECD was greater than the measured RECD, and there was considerable individual variability in the differences between average RECD and measured RECD.

Figure 5:
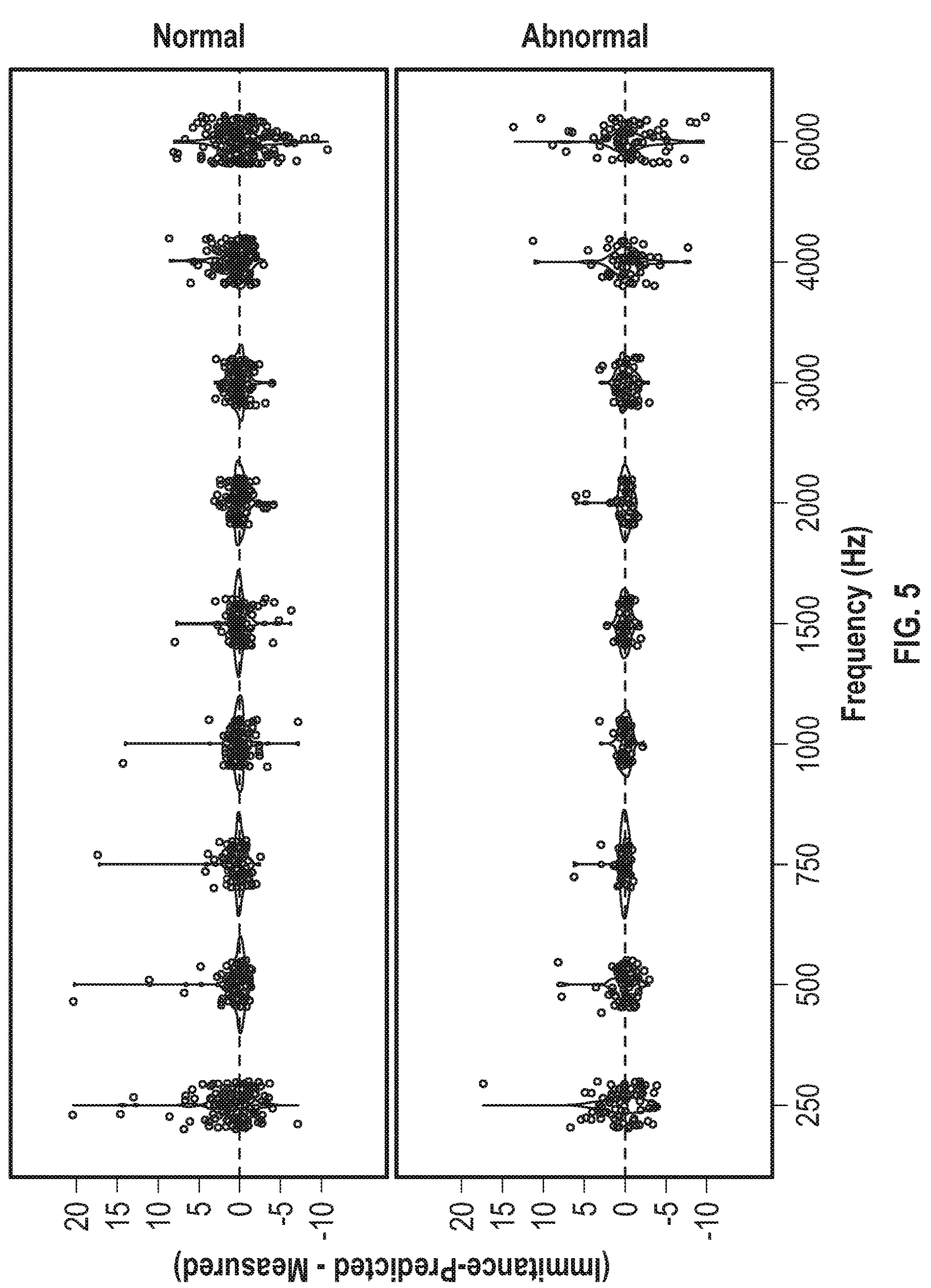
FIG. 5 is a graph showing violin plots of the differences between immittance-predicted and measured RECD in dB plotted by frequency for normal middle ear status (top panel) and abnormal middle ear status (bottom panel).

FIG. 5 shows the difference between immittance model predicted RECD and measured RECD for the participants in the study to represent the magnitude of estimation errors that would be made using the immittance model predicted RECD instead of measured RECD for this sample. For both normal and abnormal middle ear status, the distribution of differences is within the range of +/−5 dB between the immittance-predicted RECD and measured RECD for each subject across the frequency range. As with the differences between average RECD and measured RECD, the largest differences between the immittance-predicted RECD and measured RECD were at 250 Hz and 6000 Hz, though the distribution of errors for the immittance-predicted RECD were more evenly distributed around 0 dB than for average RECD.

Figure 6:
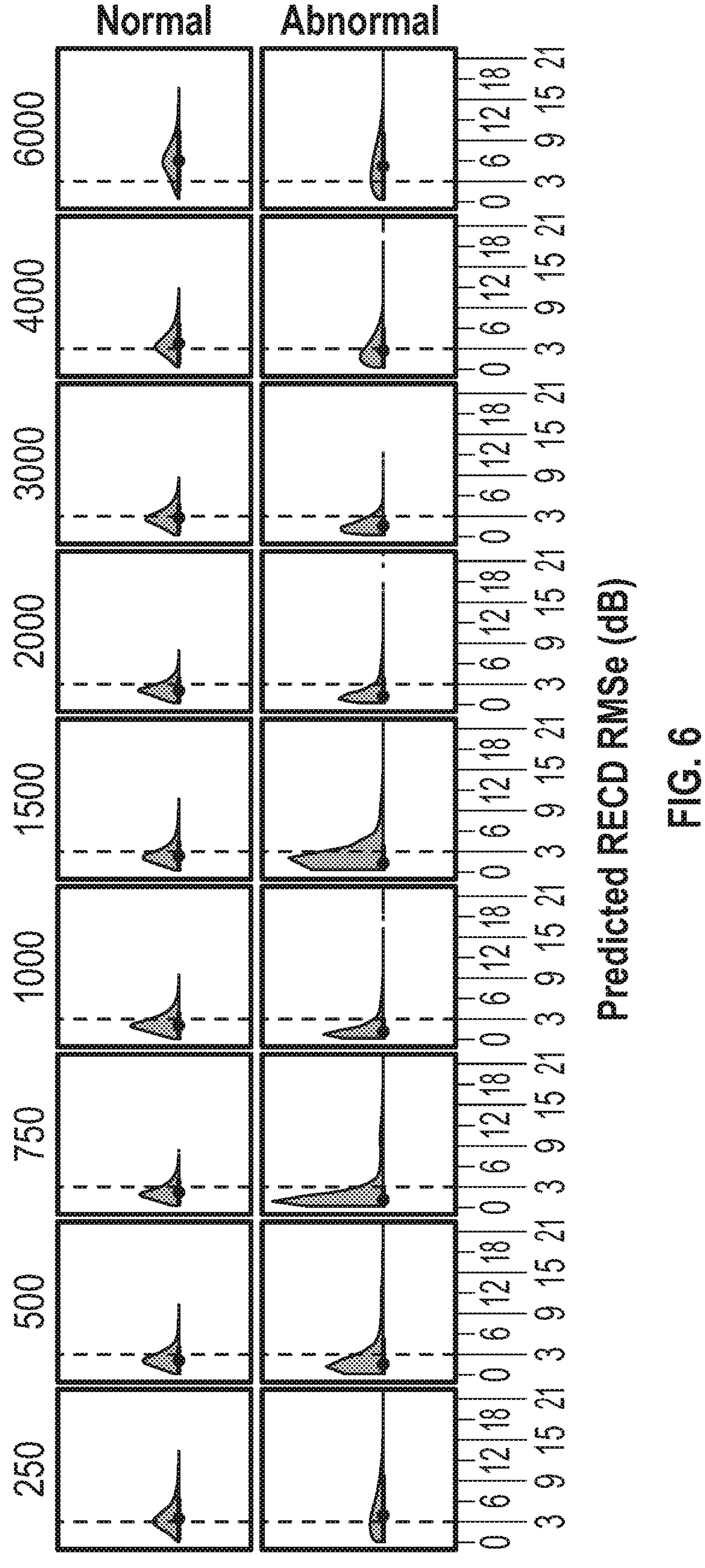
FIG. 6 is a graph showing the root-mean-square error (RMSe) of approximation across frequency (columns) and middle ear status (normal—top row; abnormal—bottom row).

To further quantify the absolute magnitude of error and uncertainty from the immittance-predicted RECD, FIG. 6 depicts the root mean square error (RMSe) of immittance-predicted RECDs by frequency and middle ear status. The RMSe ignores whether errors are positive or negative to provide an overall estimate of accuracy. The dashed line is at 3 dB, which was chosen as a meaningful degree of accuracy based on previous studies of test-retest reliability of the RECD procedure. An RMSe of 3 dB or less would indicate a good degree of accuracy between predicted and actual RECD, while an RMSe greater than 3 dB would indicate a prediction outside of the test-retest reliability for measured RECD. For children with normal middle ear status, the RMSe of the predicted RECD fell within test-retest reliability from 250 Hz-4000 Hz with larger RMSe at 6000 Hz. For children with abnormal middle ear function, the distribution of RMSe had a much larger range indicating greater uncertainty when the middle ear status is abnormal for the model predictions of RECD.

The width of the RMSe represents the distribution of values in the posterior distribution by frequency and middle-ear status and is shown in Table 2 for the average-RECD model and immittance-predicted RECD model. For both models, the RMSe for frequencies between 500 Hz-3000 Hz was less than 3 dB for children with either normal or abnormal middle-ear status, The RMSe for the immittance-predicted model was smaller by approximately 1 dB for from 500 to 6000 Hz than the average-RECD model.

TABLE 2

Root-mean-square error (RMSe) in dB by model and tympanic membrane status across frequency

| Model | ME Status | 250 | 500 | 750 | 1000 |
|---|---|---|---|---|---|
| Average-only | Normal | 4.49 [4.34, 4.63] | 3.81 [3.68, 3.94] | 3.78 [3.64, 3.91] | 3.76 [3.63, 3.88] |
| Immittance | Normal | 4.36 [4.06, 4.73] | 3.03 [2.73, 3.47] | 2.75 [2.45, 3.09] | 2.78 [2.5, 3.16] |
| Average-only | Abnormal | 4.95 [4.61, 5.34] | 4.17 [3.72, 4.43] | 4.07 [3.65, 4.39] | 3.99 [3.59, 4.31] |
| Immittance | Abnormal | 5.12 [4.34, 5.86] | 2.86 [2.41, 3.63] | 1.95 [1.63, 2.27] | 1.93 [1.64, 2.36] |

| 1500 | 2000 | 3000 | 4000 | 6000 |
|---|---|---|---|---|
| 3.87 [3.73, 4.01] | 3.66 [3.54, 3.79] | 3.83 [3.69, 3.97] | 4.38 [4.23, 4.51] | 6 [5.88, 6.17] |
| 3.08 [2.73, 3.68] | 2.58 [2.39, 2.75] | 3 [2.81, 3.2] | 4.16 [3.88, 4.46] | 6.72 [6.29, 7.01] |
| 3.96 [3.62, 4.3] | 3.93 [3.62, 4.34] | 4.08 [3.75, 4.45] | 4.89 [4.58, 5.27] | 5.62 [5.24, 6.01] |
| 2.12 [1.61, 2.78] | 1.91 [1.61, 2.27] | 2.66 [2.29, 3.07] | 4.28 [3.65, 5.1] | 6.51 [5.49, 7.32] |

Figure 7:
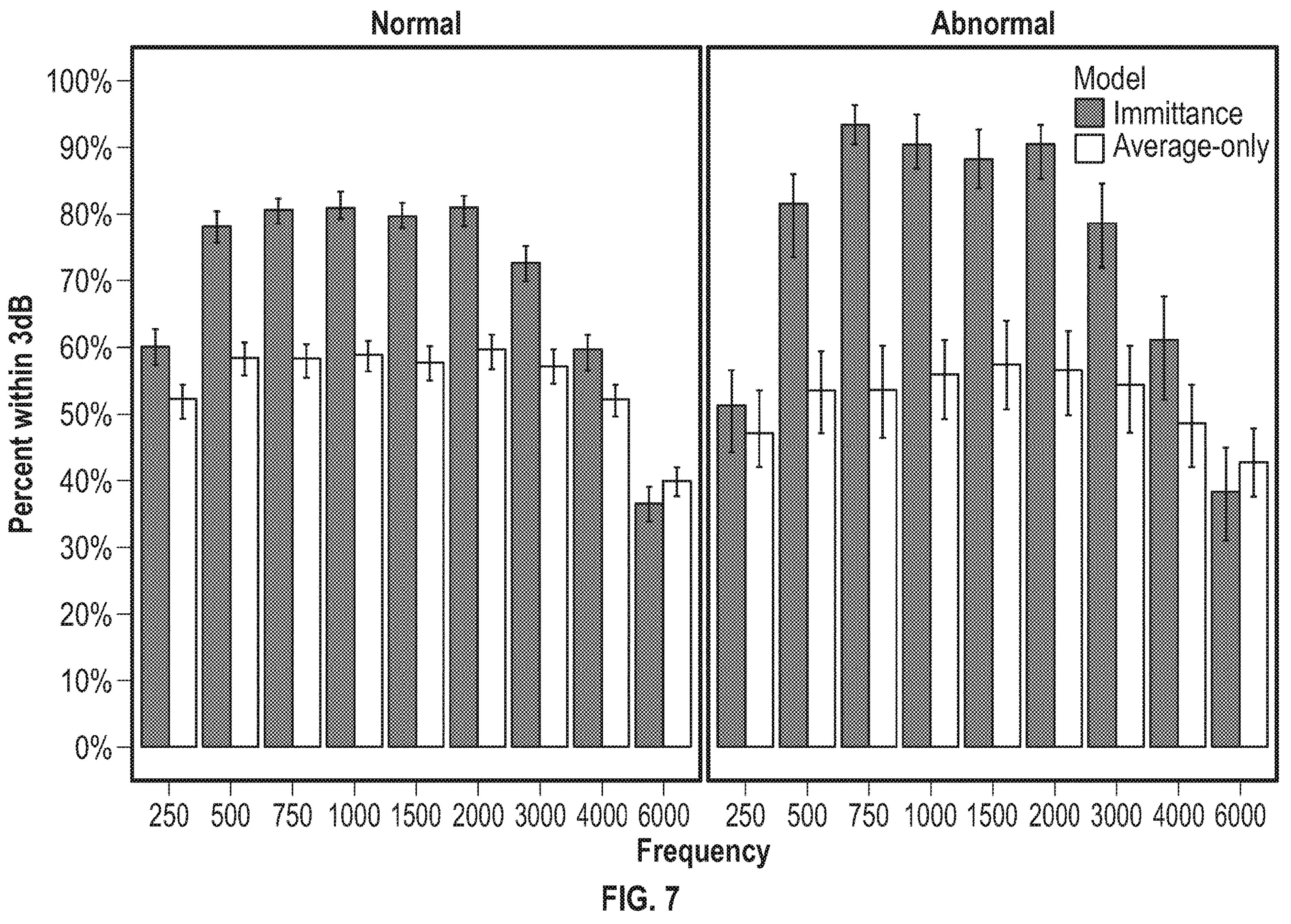
FIG. 7 is a graph showing the percent of ears within 3 dB of the measured real-ear-to-coupler difference (RECD) by frequency (Hz) for immittance-predicted RECD (dark gray bars) and average RECD (white bars).

The proportion of ears where each model would produce an estimate within 3 dB of the measured RECD was estimated to further assess the relative clinical accuracy of immittance-predict RECD compared to average RECD. FIG. 7 shows the percentage of cases within 3 dB by frequency for each model by middle-ear status.

Table 3 shows the proportion of cases within 3 dB for each model and middle-ear status by frequency. For children with either normal or abnormal middle-ear status, the immittance-predicted RECD resulted in a higher proportion of cases within 3 dB of the measured RECD than the average RECD at every frequency except 6000 Hz. For children with normal middle ear status, the average RECD model was within 3 dB in 54.8% [89% CI 53.7, 55.3] of ears across frequency, whereas the proportion of ears within 3 dB for the immittance-predicted RECD was 69.6% [89% CI 68.9, 70.4]. Similarly for children with abnormal middle ear status, the average RECD model was within 3 dB in 50.6% of ears [89% CI 48.9, 51.8] whereas the immittance-predicted RECD was within 3 dB of measured RECD in 74.4% of ears [89% CI 71.8, 76.2]. Overall, the immittance-predicted RECD was within 3 dB of the measured RECD more often than the average RECD.

TABLE 3

Proportion of predictions within 3 dB of observed

| Model | TM | 250 | 500 | 750 | 1000 | 1500 | 2000 | 3000 | 4000 | 6000 |
|---|---|---|---|---|---|---|---|---|---|---|
| Average-only | Normal | 52.39 [0.49, 0.55] | 58.35 [0.56, 0.61] | 58.24 [0.55, 0.6] | 58.8 [0.56, 0.61] | 57.63 [0.55, 0.6] | 59.8 [0.57, 0.62] | 57.24 [0.55, 0.6] | 52.34 [0.5, 0.54] | 39.87 [0.38, 0.42] |
| Immitance | Normal | 60.13 [0.57, 0.63] | 78.17 [0.76, 0.8] | 80.62 [0.79, 0.82] | 80.9 [0.79, 0.83] | 79.68 [0.78, 0.82] | 81.07 [0.78, 0.83] | 72.72 [0.7, 0.75] | 59.8 [0.57, 0.62] | 36.53 [0.34, 0.39] |
| Average-only | Abnormal | 47.06 [0.42, 0.54] | 53.68 [0.47, 0.6] | 53.68 [0.46, 0.6] | 55.88 [0.49, 0.61] | 57.35 [0.51, 0.64] | 56.62 [0.5, 0.62] | 54.41 [0.47, 0.6] | 48.53 [0.42, 0.54] | 42.65 [0.38, 0.48] |
| Immitance | Abnormal | 51.47 [0.44, 0.57] | 81.62 [0.74, 0.86] | 93.38 [0.9, 0.96] | 90.44 [0.87, 0.95] | 88.24 [0.84, 0.93] | 90.44 [0.85, 0.93] | 78.68 [0.72, 0.85] | 61.03 [0.52, 0.68] | 38.24 [0.31, 0.45] |

Figure 8:
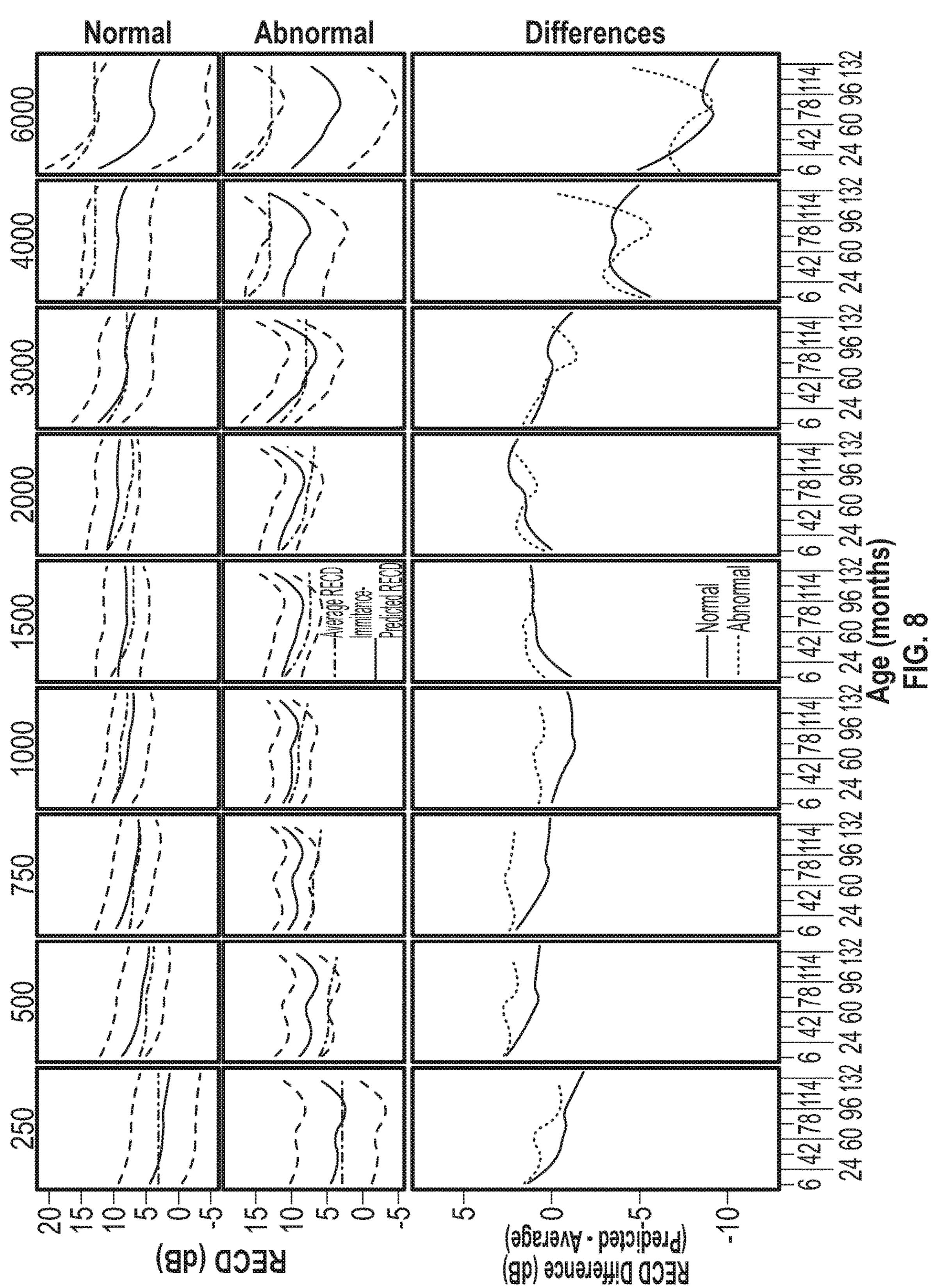
FIG. 8 is a graph showing the immittance-predicted RECD as a function of age in months.

To examine the applicability of immittance-predicted RECD across the age range where RECD may not be able to be measured as part of the hearing-aid verification process, the immittance-predicted RECD values were predicted across age. FIG. 8 shows the immittance-predicted RECD compared to the average RECD as a function of frequency and age in months. The average RECD was within the 89% credible interval for the immittance-predicted RECD at each frequency across the age range from 6-132 months. As anticipated, both average RECD and immittance predicted RECD decrease as age increases for children with normal middle ears. For 250 Hz and frequencies above 1500 Hz, the average RECD does not change significantly after 60 months of age, whereas the immittance-model RECD for children with normal middle ear shows continued decreases across frequency consistent with maturation and growth of the ear canal. For children with abnormal middle ears, the immittance-predicted RECD shows a decrease followed by an increase across frequency that is not represented by the average RECD.

Discussion: As stated throughout the present disclosure, predictions of a child's measured RECD based on an age-based normative RECD values (average RECD model), which is the current clinical gold standard in cases where RECD cannot be measured, were compared to a model that combined age-based average RECD with 226 Hz tympanometry measures (immittance-predicted RECD model). At least some goals were to determine if incorporating tympanometric immittance data that reflect the acoustical properties of the ear canal and middle ear could improve the accuracy of hearing aid verification compared to average RECD in cases where the RECD cannot be individually measured and in cases where using average RECD would lead to hearing aid fitting errors, including cases of tympanostomy tubes or tympanic membrane perforation. A Bayesian statistical approach has been used to help quantify the probabilities and magnitude of clinical errors that exist from using average RECD or immittance-predicted RECD measures for children with both normal abnormal middle ear statuses.

It has been found that the immittance-predicted RECD model that incorporated 226 Hz tympanometry data from each child led to a greater proportion of predictions within 3 dB of a child's measured RECD than a model that used only the average RECD values based on the child's age. The average RECD model resulted in predictions of RECD that were within 3 dB in approximately 54% of cases with normal middle ears and 50% of cases with abnormal middle ear, whereas the immittance-predicted RECD was within 3 dB for 69.6% of cases with normal middle ears and 74% of cases with abnormal middle ears. Across frequencies, both average RECD and immittance-predicted RECD estimates were within 3 dB of measured RECD except at 250 Hz and 6000 Hz where the differences and estimates of uncertainty were larger. These findings suggest that incorporating available immittance data from 226 Hz tympanometry for an individual child leads to more accurate estimates of ear-canal acoustics for most frequencies than relying on an average RECD for the child's age by itself regardless of middle ear status.

The finding that estimates of RECD from the immittance-predicted RECD model were more accurate than using the average RECD is consistent with predictions based on acoustical modelling from previous studies. Acoustic characteristics of the ear canal and middle ear are known to affect real-ear-to-coupler differences due to individual differences in impedance that exist across children. Individual differences in ear canal volume and middle ear impedance can lead to significant differences in ear canal acoustics, particularly when the ear canal is occluded by an earmold. These analyses provide further support for the use of hearing-aid verification using average RECD when a child's RECD cannot be individually measured. Importantly, the immittance-predicted model as disclosed in the aspects and/or embodiments of the present disclosure further improved upon those predictions compared to the average RECD model for children with normal or abnormal middle ear status. Thus, there has been shown a noted improvement and advantage in using the presently disclosed models.

Although the immittance-predicted RECD has been shown to be more accurate than using an average RECD alone, particularly for children with abnormal middle ear status, the results also show that using an average RECD also produces reasonable predictions of RECD in 50% of ears regardless of middle ear status. Recent studies of hearing aid fitting errors in children who did not consistently receive either in situ or simulated in situ hearing-aid verification suggest that more than half of children had a fitting error in one ear that was 5 dB or greater from 500 Hz-4000 Hz. Both the average RECD and immittance-predicted RECD model produced estimates of ear-canal acoustics that would have led to lower fitting errors had they been used as part of the hearing aid verification process, even for children with abnormal middle ear status at the time of hearing aid verification. Immittance-predicted RECD offers an option with intermediate accuracy between the current gold standard of in situ or simulated in situ hearing-aid verification with a measured RECD and using an average RECD, but the fitting errors from average RECD observed in a study were smaller than the fitting errors for children who did not have their hearing aids fitted with validated verification approaches in previous studies.

Clinical guidelines currently advise against using average RECD values in cases where children have abnormal middle ear function, tympanic membrane perforation, or tympanostomy tubes. This recommendation is based on the fact that the normative sample of children from which average RECD were derived have had intact tympanic membranes and normal middle ear function. However, the average RECD was within 3 dB of the measured RECD in half of the cases for children with abnormal middle ears and adding clinical immittance data improved the proportion of ears within 3 dB to almost 75%. This shows additional advantages of utilizing the immittance data in addition to the average RECD age-based data, which is a part of aspects and/or embodiments of the present disclosure. Thus, it is to be appreciated that the use of immittance-predicted RECD in cases where in situ verification or measured RECD is not plausible is an improvement over the art.

For the average RECD and immittance-predicted RECD models, the estimation of measured RECD at 6000 Hz was generally poorer than other frequencies, indicated by large RMSe values, broad credible intervals, and less than half of cases with 3 dB of the measured RECD. In general, the measured RECD values at 6000 Hz for the sample of children who contributed data to these analyses were lower than the average RECD normative values from the published literature. This discrepancy between the measured RECD and average RECD at 6000 Hz is likely related to the presence of standing waves in the ear canal at the position of the probe microphone related to the cancellation of forward-moving sound waves and sound waves reflected from the tympanic membrane. As the bandwidth of hearing aids increases, the impact of these discrepancies at 6000 Hz for hearing-aid verification are likely to affect estimates of hearing aid output in clinically meaningful ways. The application of wideband acoustic immittance, which characterizes the middle ear across a broader range of frequencies than 226 Hz tympanometry, and the use of wideband RECD may help to improve the relationship between immittance characteristics and predictions of ear-canal acoustics at higher frequencies.

One main improvement and/or advantage that can be understood from the present disclosure is that incorporating immittance data from 226 Hz tympanometry can improve predictions of RECD compared to the average RECD, which has implications for clinical practice. Previous research suggests that the average RECD may be used in 25-30% of clinical visits for hearing-aid verification for infants and young children. In those instances, generating a predicted RECD based on the child's 226 Hz tympanometry provides a more accurate estimate of ear canal acoustics than using the average RECD alone for children regardless of middle ear status, but particularly for children with abnormal middle ear function. Because 226 Hz tympanometry is easy to obtain and widely available, such as via many clinical devices, apparatuses, and/or tools, this approach warrants further exploration in a clinical context to develop tools and assess the impact of these predictions on the accuracy of hearing aid fittings. While the immittance-predicted RECD produced more precise estimates of measured RECD than average RECD, the effects of greater precision in predictions of RECD on speech audibility are likely to depend on degree of hearing loss.

The 226 Hz tympanometry data that was incorporated into RECD predictions in the full model characterizes the outer and middle ear at a single, low frequency. The RECD is a broadband measurement and may benefit from the use of a broadband characterization of the outer and middle ear using available techniques such as wideband acoustic immittance. Tympanometry also pressurizes the ear canal to characterize the admittance and relative pressure of the middle ear, but RECD measurements are not completed under pressurized conditions. Pressurizing the ear canal can influence the acoustic characteristics and sound level in the ear canal. Wideband acoustic immittance can be conducted at ambient pressure like the RECD and may more accurately predict the RECD. Although the results of the full model suggest a substantial improvement across frequencies based on pressurized 226 Hz tympanometry, future research should consider the impact of unpressurized wideband estimates of outer and middle ear function to further improve predictions of measured RECD and the accuracy of children's hearing aid fittings.

Therefore, it should be appreciated that the present disclosure has shown that adding immittance data from 226 Hz tympanometry improves predictions of measured RECD compared to the average RECD alone. Immittance data and average RECD data can be used to generate Bayesian statistical models to predict each child's measured RECD. The results of the model suggest that the immittance-predicted RECD model produces smaller differences and a larger proportion of estimates within 3 dB of the measured RECD than the average RECD model for children with normal and abnormal middle ear statuses. The immittance-predicted model produced estimates within 3 dB for approximately 70% of cases with normal middle ear function and 74% of cases with abnormal middle ear function, whereas the average RECD model produced estimates within 3 dB in approximately 50% of cases regardless of the child's middle ear status. Both average RECD and immittance-predicted RECD produced differences from measured RECD that were smaller than if hearing aid verification had not been conducted. Clinical immittance measures can improve the accuracy of predictions of RECD when the RECD cannot be measured compared to using average RECD data in children.

Yet additional examples are provided for the present disclosure. Further studies have included using otoscopy to confirm the absence of occlusive cerumen or other ear-canal anomalies. Wideband acoustic immittance was conducted once in each ear, and measures of ear canal volume, peak static admittance at 226 Hz, tympanometric peak pressure, and ambient absorbance nearest to 0 daPa were extracted. Wideband acoustic immittance measures were repeated only if the child was noisy during the measurement. Middle ear status was classified as normal or abnormal based on ear canal volume, admittance, and tympanometic peak pressure using the 226 Hz tympanogram derived from the pressurized wideband acoustic immittance measurement. An equivalent ear-canal volume of 0.4-2.0 $cm^3$, admittance of ≥0.3 mL, and tympanometric peak pressure ≥−150 daPa on 226 Hz tympanometry were the criteria for normal middle ear status. Abnormal middle ear status was given to data from ears where one or more of the equivalent volume, admittance, and/or tympanometric peak pressure were outside of the normal range.

Individual wideband RECDs (wRECDs, which is an instantiation of the RECD that can characterize ear canal acoustics at frequencies above 6000 Hz) were measured for all children. The participant was seated approximately 2-feet from the probe microphone verification system. A flexible probe microphone was placed into the ear using the constant insertion method, where the probe is placed in the ear canal approximately 10 mm past the medial termination of a pediatric insert foam plug. The transducer that delivered sound into the ear canal was connected to a foam insert. A Verifit 2 default RECD stimulus of 60 dB SPL pink-shaped noise was delivered to the ear through the insert foam tip for approximately 10 seconds or until the response stabilized. The same broadband noise was presented via the transducer to a the 0.4 $cm^3$ coupler used for hearing aid verification. The wRECD was the difference between the 0.4 $cm^3$ coupler response and the response measured in the child's ear canal. Frequency-specific age-based average wRECD data for each child were based on the child's age at the time of the study visit taken from the normative RECD data in Audioscan Verifit 2.

Again, Bayesian frame is utilized and models can be constructed using the Stan programming language through the cmdstanr and brms packages in R statistical computing software. To address questions about the potential benefits of incorporating individual measures of ear-canal acoustics from standard clinical tympanometry as well as wideband acoustic immittance to enhance predictions of the child's wRECD, the process constructed three models to predict each child's measured wRECDs. The average age-based wRECD model included population-level effects of frequency, age, and average wRECD. The 226 Hz admittance wRECD model was generated as a replication of the model completed in our previous study and included the same effects of the average age-based wRECD model but added data from 226 Hz tympanometry derived from the wideband acoustic immittance measure including ear-canal volume (ECV), the peak static admittance nearest to 226 Hz, and interaction terms for average wRECD×frequency and middle-ear status×frequency, and middle-ear status×absorbance. The wideband absorbance wRECD model included the same predictors as the 226 Hz admittance model but included an effect for frequency-specific absorbance at ambient pressure in place of the 226 Hz admittance at tympanometric peak pressure. All models included varying (group-level) effects of frequency and middle-ear status by subjects' individual ears. We estimated distributional effects of variance ($\sigma$) and degrees of freedom ($\nu$) with varying effects of frequency and middle-ear status.

Comparisons were made for the wideband absorbance wRECD, 226 Hz admittance wRECD, and average age-based wRECD models using Pareto smoothed importance sampling leave-one-out cross-validation (PSIS-LOO) to estimate the expected log predictive density (ELPD) and evaluate and compare the fit of the three models to the data. A difference in PSIS-LOO ELPD of 3-5 times greater than the standard error (SE) is considered a significant improvement. Comparing our models, our wideband absorbance wRECD model was a significantly better fit to the data relative to the average age-based wRECD model with a difference in ELPD of 1452.2 (SE of 55.6) in favor of the wideband absorbance wRECD model. However, ELPD was equivocal between the 226 Hz admittance wRECD model and the wideband absorbance wRECD model (ELPD difference: 1.2, SE: 8.1) consistent with no differences in model fit between the two models that included individual immittance data.

Figure 9:
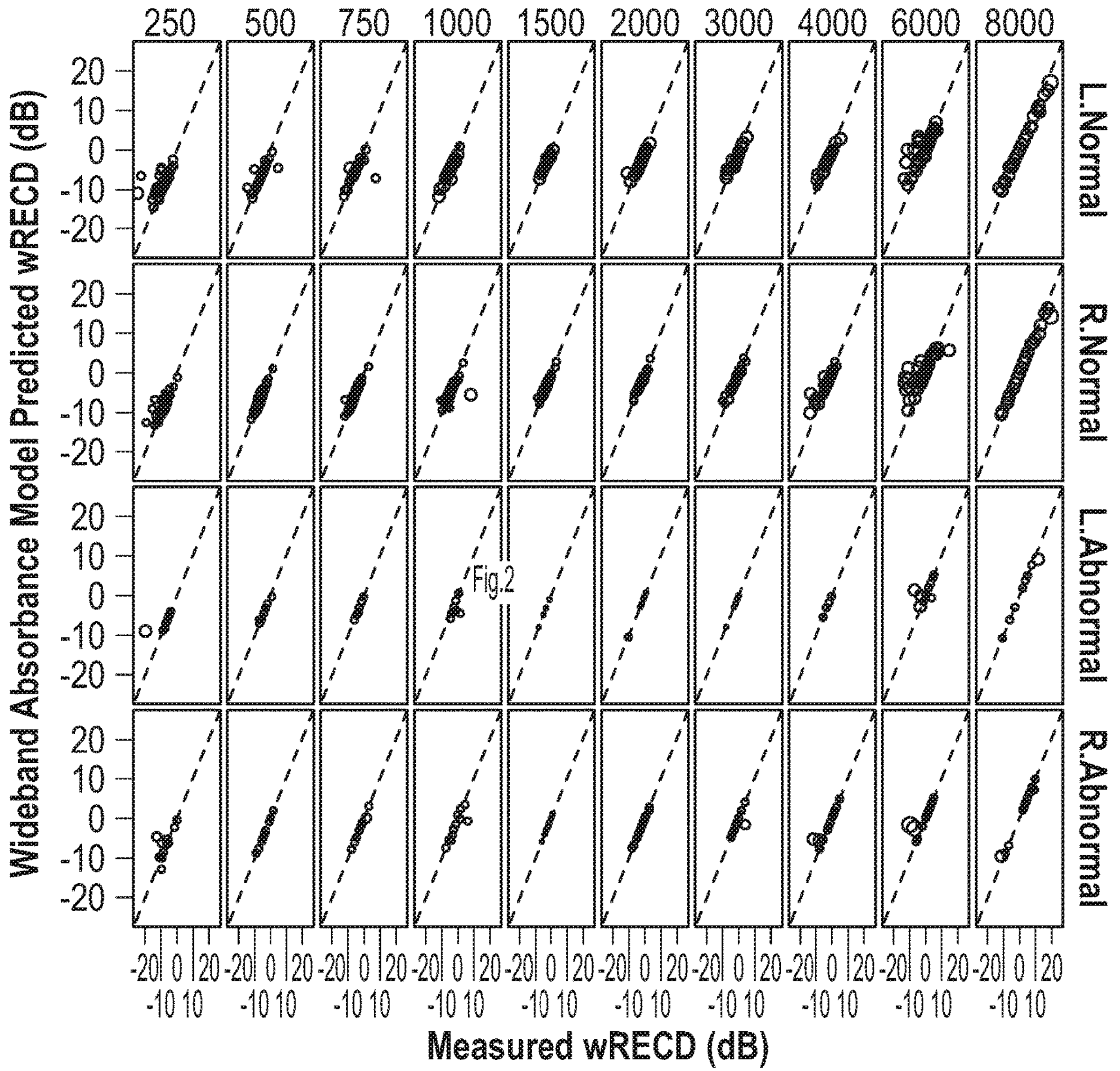
FIG. 9 is a graph showing wideband absorbance wRECD versus measured wRECD by frequency, ear (R=Right, L=Left), and middle-ear status (Normal vs. Abnormal).

FIG. 9 shows the wideband absorbance wRECD model predictions as a function of the measured wRECD. In general, the model predictions of wRECD were concentrated along the diagonal for frequencies from 250 Hz-4000 Hz for children with normal and abnormal middle ear function, indicating good agreement between model predictions and measured wRECD with low uncertainty. Greater uncertainty of model estimates was observed at 6000 Hz and 8000 Hz as evidenced by larger circles and circles off the diagonal line. The mean difference between ears was 0.08 dB (SE: 3.4 dB), so additional figures display model predictions collapsed across ears of the same participants. As shown in FIG. 9, perfect prediction is indicated by the diagonal dashed line. Uncertainty is represented by the width of the 89% highest-density credible interval around the prediction and is depicted as the size of the circles.

Figure 10:
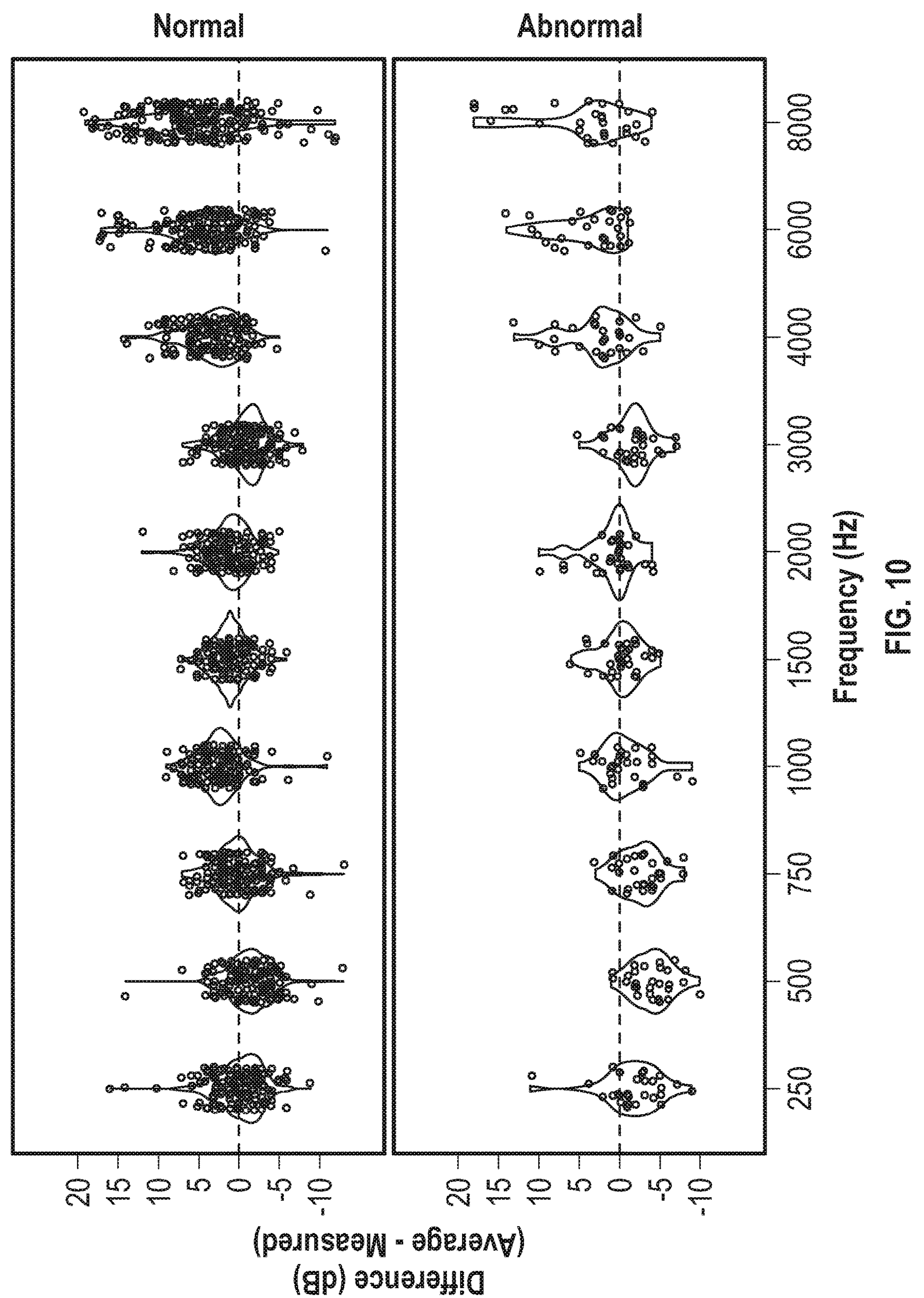
FIG. 10 is a graph showing violin plots of the difference between the average age-based wRECD model and measured wRECD by frequency and middle ear status (upper panel—normal middle ear status; lower panel abnormal middle ear status).

FIG. 10 shows the differences between the average wRECD and measured wRECD as a function of frequency and middle ear status. The interquartile range of the differences between the average age-based wRECD model predictions and measured wRECD were within +/−5 dB for frequencies from 250 Hz-3000 Hz and +/−10 dB for 4000 Hz-6000 Hz. As shown in FIG. 10, circles represent individual differences at each frequency between model predictions and measured wRECD. The violin plot provides a symmetrical representation of the distribution of values at each frequency with the vertical boundaries representing the range of differences.

Figure 11:
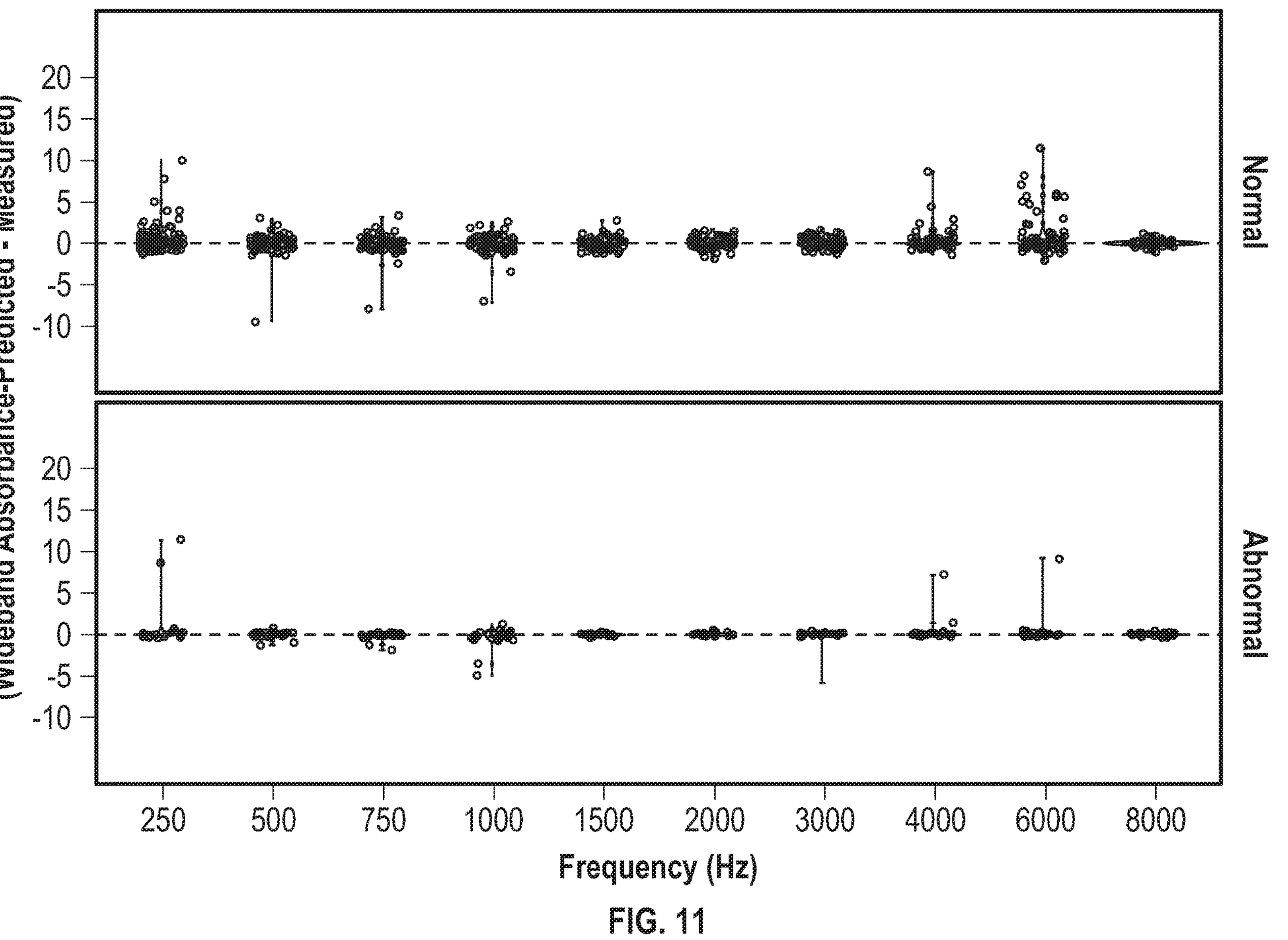
FIG. 11 is a graph showing violin plots of the difference between the wideband absorbance wRECD model and measured wRECD by frequency and middle ear status (upper panel—normal middle ear status; lower panel abnormal middle ear status).

FIG. 11 shows the differences between the wideband absorbance wRECD model and measured wRECD as a function of frequency and middle ear status. The differences between the average age-based wRECD model predictions and measured wRECD were within +/−2 dB for frequencies from 250 Hz-8000 Hz. The wideband absorbance model resulted in much smaller interquartile ranges for predictions of each child's measured wRECD than the average age-based wRECD model. Circles represent individual differences at each frequency between model predictions and measured wRECD. The violin plot provides a symmetrical representation of the distribution of values at each frequency with the vertical boundaries representing the range of differences.

Figure 12:
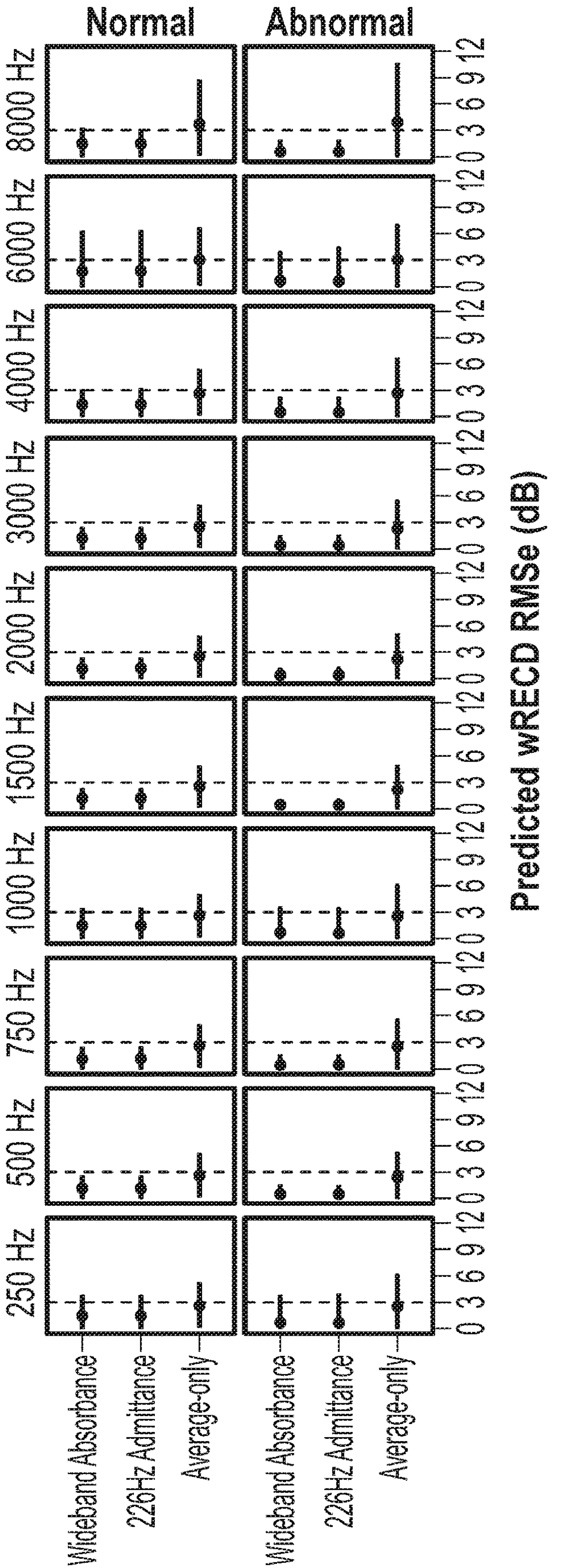
FIG. 12 is a comparison of model root-mean-square error (RMSe) by frequency (columns) and middle ear status (upper panel—normal middle ear status; lower panel abnormal middle ear status.

To further quantify the differences between the three models, the root mean square error (RMSe) of predicted wRECDs for predicting each child's measured RECD was calculated by frequency and middle-ear status. A criterion of 3 dB was chosen as a meaningful degree of accuracy based on previous studies of test-retest reliability of the RECD and wRECD procedures. FIG. 12 shows the RMSe by frequency and model by middle ear status. The wideband absorbance, 226 Hz admittance, and average age-based wRECD models are shown within each panel. Points represent median estimates, horizonal bars indicate the 89% highest-density credible interval around the median estimates.

Figure 13:
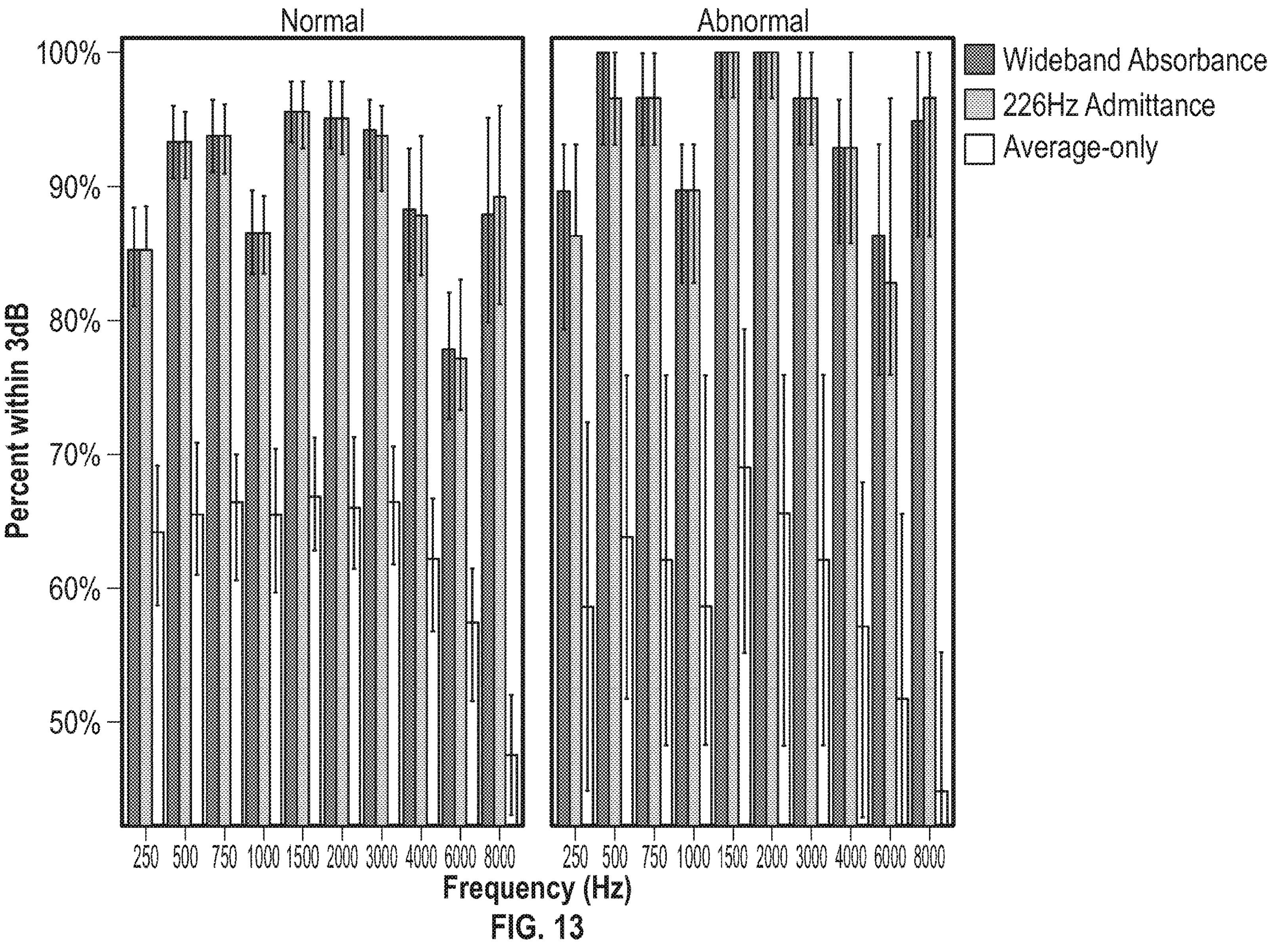
FIG. 13 shows bar plots indicating the percentage of cases for each model within 3 dB of the measured wRECD by frequency and middle ear status (left panel—normal middle ear status; right panel—abnormal middle ear status).

An RMSe of 3 dB or less indicates a degree of accuracy between predicted and actual wRECD within the limits of test-retest, while an RMSe greater than 3 dB would indicate a prediction outside of the test-retest reliability for measured wRECD. For children with normal or abnormal middle ear status, the RMSe of the 226 Hz admittance and wideband absorbance wRECD models fell within test-retest reliability of the measured wRECD from 250 Hz-6000 Hz with larger errors at 8000 Hz for both models. For the average age-based wRECD model, the RMSe was larger and had a broader confidence interval range indicating greater uncertainty in wRECD estimates for both normal and abnormal middle ear status groups. The RMSe for the 226 Hz admittance and wideband absorbance wRECD models were smaller than the average age-based wRECD model by approximately 1 dB at 500 Hz, 750 Hz, 1000 Hz, 1500 Hz, 2000 Hz, and 3000 Hz for both middle ear status groups. To further compare the accuracy of the three models for predicting the measured wRECD, the proportion of cases where each model was within 3 dB of each child's measured wRECD was calculated. FIG. 13 shows the proportion percentage of cases for each model that were within 3 dB of each child's measured wRECD. Dark gray bars represent the wideband absorbance model, light gray bars represent the 226 Hz admittance model, and white bars represent the average wRECD predicted model. The whiskers on each bar represent the 89% credible interval for model predictions at each frequency.

Figure 14:
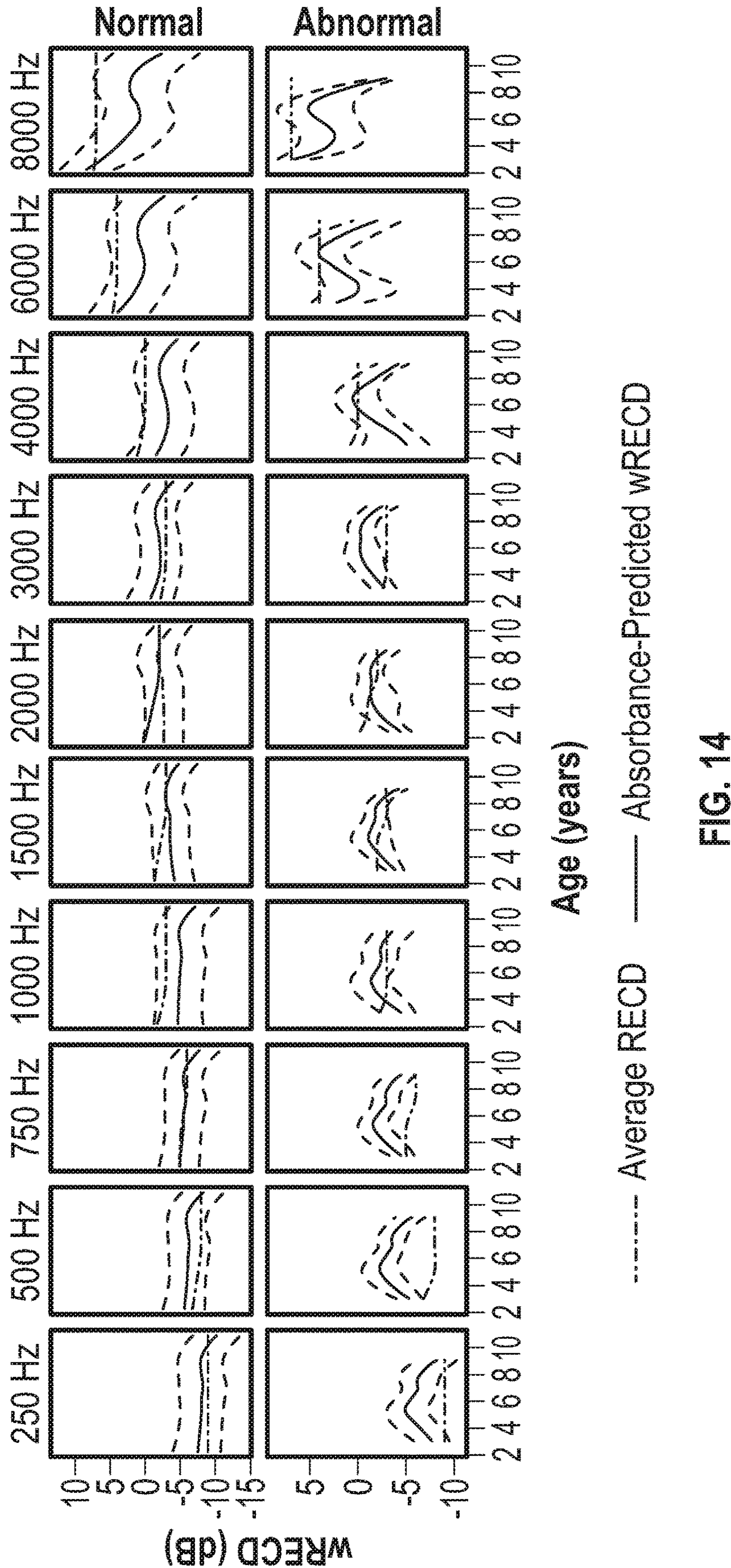
FIG. 14 shows graphs of wideband absorbance wRECD and average age-based wRECD as a function of age in years by frequency (columns) and middle ear status (upper row—normal middle ear status; lower row—abnormal middle ear status).

For children with normal middle-ear status, the wideband absorbance model had a higher proportion of cases within 3 dB of the measured wRECD at every frequency except 6000 Hz than the average age-based wRECD model. The average age-based wRECD model was within 3 dB in 62.3% [89% CI 60.7, 63.7] of cases across frequency, whereas the proportion of cases within 3 dB for the wideband absorbance model was 90.1% of cases [89% CI 89.0, 91.4] and 90.0% of cases [89% CI 88.6, 91.1] were within 3 dB with the 226 Hz admittance model. A larger proportion of cases had smaller errors by incorporating individual immittance data into predictions of wRECD compared to using an average wRECD. FIG. 14 contrasts the average wRECD and wideband absorbance wRECD across age by frequency and middle ear status.

As shown in FIG. 14, the dashed lines in each panel represent the range of the 89% credible interval for the wideband immittance-predicted wRECD model. The average wRECD and wideband absorbance wRECD model had reasonable concordance of average values between 250 Hz-3000 Hz, but the average wRECD tended to be higher than the wideband absorbance wRECD from 4000 Hz-8000 Hz for both middle ear status groups with a broader range of the 89% credible interval consistent with greater model uncertainty.

Figure 15:
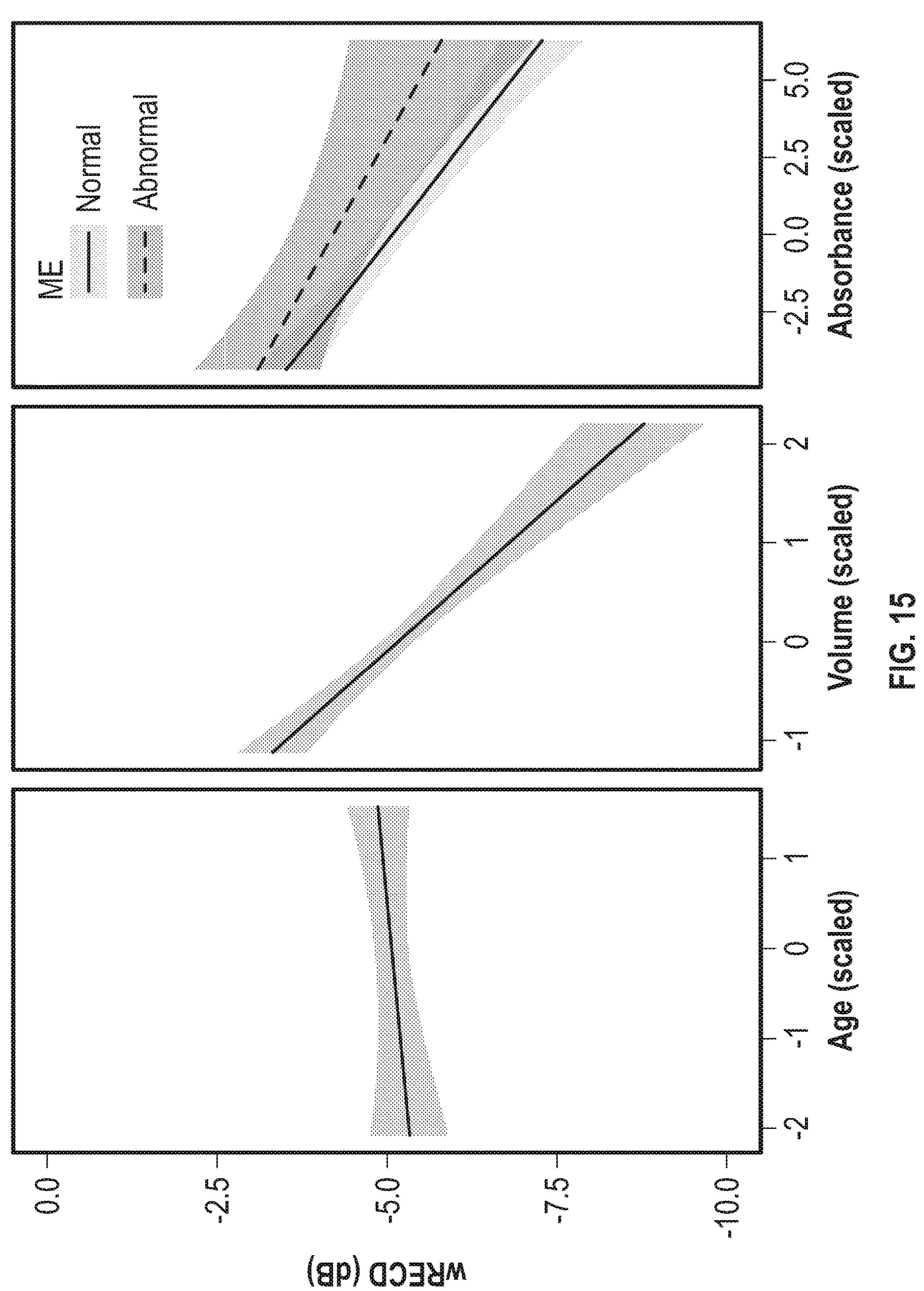
FIG. 15 shows graphs of the conditional effects of age (left panel), equivalent ear-canal volume (middle panel), and absorbance (right panel) on wRECD from the wideband absorbance wRECD model.

The conditional effects of age, equivalent ear-canal volume, and absorbance collapsed across frequency from the wideband absorbance model are shown in FIG. 15. As shown in the figure, the solid line represents the average effect of age and equivalent ear canal volume for all participants and the effect of absorbance for children with normal middle ear function. The dashed line in the absorbance panel represents the conditional effect of absorbance on RECD for children with abnormal middle ear function. The shaded area around each line represents the 89% credible interval around the average from the model.

There was a negative relationship between wRECD and age, with wRECD values decreasing as age increased. Likewise, wRECD decreased as absorbance and ear-canal volume increased. Absorbance showed the same negative relationship with wRECD in both middle ear status groups, but the 89% credible interval was larger for the children with abnormal middle ear function indicating greater model uncertainty for children in that group. These trends are consistent with the anticipated relationships between these variables and the wRECD from previous studies.

Therefore, as summary, data extracted from wideband acoustic immittance measurements from 150 children with intact tympanic membranes was used to construct three Bayesian statistical models using measured wRECD: a wideband absorbance wRECD model, a 226 Hz admittance wRECD model, and an age-based average age-based wRECD model. The prediction hypothesis was that the wideband absorbance wRECD model would provide the most accurate estimates of the child's measured wRECD by characterizing the impedance of the ear at a broader range of frequencies at ambient pressure. The 226 Hz admittance wRECD model was predicted expected to provide more accurate estimates of wRECD than the age-based average age-based wRECD model. However, these predictions expectations were only partially confirmed. The results suggest that model predictions of wRECD that incorporate individual measures of immittance from either wideband absorbance or 226 Hz tympanometry provide an estimate of wRECD that is within 3 dB of the child's measured RECD in approximately 90% of cases (FIG. 5). In this analysis, the wideband absorbance measures did not improve the accuracy or reduce the uncertainty of model predictions measured wRECD compared to the 226 Hz admittance model. The age-based average age-based wRECD model produced estimates of measured wRECD that were within 3 dB in approximately 62% of cases. Incorporating individual immittance measures to predict wRECD can improve the accuracy and reduce uncertainty of predictions of the wRECD transform that is used in hearing aid fitting for infants and young children when a child's ear-canal acoustics cannot be directly measured. This approach has the potential to improve the accuracy of hearing aid fittings for infants and young children when immittance data are available, but individual wRECD measures cannot be completed due to limited child cooperation or other factors.

The systems, methods, and/or apparatus as disclosed herein provide numerous advantages for providing modeling, training, and/or application for the non-invasive testing of the estimation and/or effectiveness of hearing aids. This includes, but it not limited to, the use of 226 Hz tympanometry or wideband acoustic immittance measurements to obtain variable data from a patient, such as by use of a clinical device, tool, or apparatus, which are currently used. The clinical devices can operatively include or otherwise be connected to computer readable medium, which can include machine learning networks that can be trained to identify and evaluate the collected data. Upon collection, the computer readable medium can provide outputs of the immittance-predicted RECD. Such outputs can be on or at the clinical device, which provides for a numerical estimation of the effectiveness of the hearing aid device based on both the average RECD based on age and the acoustically measured data obtained by the clinical measuring device. In addition, the clinical device can be connected, such as wired or wirelessly, to a remote device or location that includes a memory, database, computer readable medium, processors, and the like, which can be viewed at a later time for evaluation. The remote device can also be used to further train the machine learning network to provide updated and improved results for the output and estimation of immittance-predicted RECD.

As will be understood, aspects and/or embodiments disclosed herein will utilize processors, memory, instructions, and the like, and will include a machine learning model or models to identify classifiers of aspects of ear conditions and/or pathologies. Machine learning (ML) is the study of computer algorithms that can improve automatically through experience and by the use of data. It is seen as a part of artificial intelligence. Machine learning algorithms build a model based on sample data, known as "training data", in order to make predictions or decisions without being explicitly programmed to do so.

The implementation of the predicted data can utilize machine learning to train a system that can be implemented into a non-invasive clinical diagnostic/measurement device. This would allow for quick and easy determination as to the effectiveness of a hearing aid device that is more accurate than using age-based RECD alone. As noted, variables associated with 226 Hz tympanometry and/or wideband acoustic immittance could be used to train the machine learning network. The machine learning network can be trained to implement the modeling and also identify classifiers that will determine the effectiveness of the hearing aid devices by combining the modeled, acoustic measurements with the age-based RECD to provide improved results.

While it is envisioned that generally any type of ML (e.g., supervised learning, unsupervised learning, semi-supervised learning, or reinforcement learning) can be utilized by any of the aspects and/or embodiments of the present disclosure utilize supervised learning. Supervised learning (SL) is the machine learning task of learning a function that maps an input to an output based on example input-output pairs. It infers a function from labeled training data consisting of a set of training examples. In supervised learning, each example is a pair consisting of an input object (typically a vector) and a desired output value (also called the supervisory signal). A supervised learning algorithm analyzes the training data and produces an inferred function, which can be used for mapping new examples. An optimal scenario will allow for the algorithm to correctly determine the class labels for unseen instances. This requires the learning algorithm to generalize from the training data to unseen situations in a "reasonable" way (see inductive bias). This statistical quality of an algorithm is measured through the so-called generalization error.

To solve a given problem of supervised learning, one has to perform the following steps: (1) Determine the type of training examples. Before doing anything else, the user should decide what kind of data is to be used as a training set. (2) Gather a training set. The training set needs to be representative of the real-world use of the function. Thus, a set of input objects is gathered, and corresponding outputs are also gathered, either from human experts or from measurements. (3) Determine the input feature representation of the learned function. The accuracy of the learned function depends strongly on how the input object is represented. Typically, the input object is transformed into a feature vector, which contains a number of features that are descriptive of the object. The number of features should not be too large, because of the curse of dimensionality; but should contain enough information to accurately predict the output. (4) Determine the structure of the learned function and corresponding learning algorithm. For example, the engineer may choose to use support-vector machines, regression analysis, or decision trees. (5) Complete the design. Run the learning algorithm on the gathered training set. Some supervised learning algorithms require the user to determine certain control parameters. These parameters may be adjusted by optimizing performance on a subset (called a validation set) of the training set, or via cross-validation. (6) Evaluate the accuracy of the learned function. After parameter adjustment and learning, the performance of the resulting function should be measured on a test set that is separate from the training set.

As will be understood, while generally any type of SL can be utilized, the example provided herein utilized three different classification algorithms to train the model, namely the support vector machine (SVM), k-Nearest Neighbors (k-NN), and classification ensemble (ENS).

Support-vector machines (SVMs, also support-vector networks) are supervised learning models with associated learning algorithms that analyze data for classification and regression analysis. Given a set of training examples, each marked as belonging to one of two categories, an SVM training algorithm builds a model that assigns new examples to one category or the other, making it a non-probabilistic binary linear classifier (although methods such as Platt scaling exist to use SVM in a probabilistic classification setting). SVM maps training examples to points in space so as to maximize the width of the gap between the two categories. New examples are then mapped into that same space and predicted to belong to a category based on which side of the gap they fall.

The k-nearest neighbors algorithm (k-NN) is a non-parametric classification method. k-NN is a type of classification where the function is only approximated locally, and all computation is deferred until function evaluation. Since this algorithm relies on distance for classification, if the features represent different physical units or come in vastly different scales then normalizing the training data can improve its accuracy dramatically.

Classification ensemble may also be referred to as ensemble learning. Ensemble methods use multiple learning algorithms to obtain better predictive performance than could be obtained from any of the constituent learning algorithms alone. Unlike a statistical ensemble in statistical mechanics, which is usually infinite, a machine learning ensemble consists of only a concrete finite set of alternative models, but typically allows for much more flexible structure to exist among those alternatives.

The trained model and the associated machine learning and application of the model will utilize processors, modules, memories, databases, networks, and potentially user interfaces to show the results and allow changes to be made.

In communications and computing, a computer readable medium is a medium capable of storing data in a format readable by a mechanical device. The term "non-transitory" is used herein to refer to computer readable media ("CRM") that store data for short periods or in the presence of power such as a memory device. It is envisioned that the clinical tools used for collecting the acoustic measurements and/or associated processors for evaluating the data from the clinical tools could implement CRM.

One or more embodiments described herein can be implemented using programmatic modules, engines, or components. A programmatic module, engine, or component can include a program, a sub-routine, a portion of a program, or a software component or a hardware component capable of performing one or more stated tasks or functions. A module or component can exist on a hardware component independently of other modules or components. Alternatively, a module or component can be a shared element or process of other modules, programs, or machines.

The system will preferably include an intelligent control (i.e., a controller) and components for establishing communications. Examples of such a controller may be processing units alone or other subcomponents of computing devices. The controller can also include other components and can be implemented partially or entirely on a semiconductor (e.g., a field-programmable gate array ("FPGA")) chip, such as a chip developed through a register transfer level ("RTL") design process.

A processing unit, also called a processor, is an electronic circuit which performs operations on some external data source, usually memory or some other data stream. Non-limiting examples of processors include a microprocessor, a microcontroller, an arithmetic logic unit ("ALU"), and most notably, a central processing unit ("CPU"). A CPU, also called a central processor or main processor, is the electronic circuitry within a computer that carries out the instructions of a computer program by performing the basic arithmetic, logic, controlling, and input/output ("I/O") operations specified by the instructions. Processing units are common in tablets, telephones, handheld devices, laptops, user displays, smart devices (TV, speaker, watch, etc.), and other computing devices.

As noted, the clinical tool itself could include a processor, and/or the tool could be connected, either wired or wirelessly to a separate system encompassing the processing unit.

The memory includes, in some embodiments, a program storage area and/or data storage area. The memory can comprise read-only memory ("ROM", an example of non-volatile memory, meaning it does not lose data when it is not connected to a power source) or random access memory ("RAM", an example of volatile memory, meaning it will lose its data when not connected to a power source). Examples of volatile memory include static RAM ("SRAM"), dynamic RAM ("DRAM"), synchronous DRAM ("SDRAM"), etc. Examples of non-volatile memory include electrically erasable programmable read only memory ("EEPROM"), flash memory, hard disks, SD cards, etc. In some embodiments, the processing unit, such as a processor, a microprocessor, or a microcontroller, is connected to the memory and executes software instructions that are capable of being stored in a RAM of the memory (e.g., during execution), a ROM of the memory (e.g., on a generally permanent basis), or another non-transitory computer readable medium such as another memory or a disc.

In the instant case, the memory could include the machine learned classifiers and analog models, so as to fit the parameters of the model and to quickly and accurately identify the results based on the trained classifiers.

Generally, the non-transitory computer readable medium operates under control of an operating system stored in the memory. The non-transitory computer readable medium implements a compiler which allows a software application written in a programming language such as COBOL, C++, FORTRAN, or any other known programming language to be translated into code readable by the central processing unit. After completion, the central processing unit accesses and manipulates data stored in the memory of the non-transitory computer readable medium using the relationships and logic dictated by the software application and generated using the compiler.

In one embodiment, the software application and the compiler are tangibly embodied in the computer-readable medium. When the instructions are read and executed by the non-transitory computer readable medium, the non-transitory computer readable medium performs the steps necessary to implement and/or use the present invention. A software application, operating instructions, and/or firmware (semi-permanent software programmed into read-only memory) may also be tangibly embodied in the memory and/or data communication devices, thereby making the software application a product or article of manufacture according to the present invention.

The database is a structured set of data typically held in a computer. The database, as well as data and information contained therein, need not reside in a single physical or electronic location. For example, the database may reside, at least in part, on a local storage device, in an external hard drive, on a database server connected to a network, on a cloud-based storage system, in a distributed ledger (such as those commonly used with blockchain technology), or the like.

It is envisioned that the machine learned model and any of the training of the same could include cloud computing. Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service.

A cloud computing environment is service oriented with a focus on statelessness, low coupling, modularity, and semantic interoperability. At the heart of cloud computing is an infrastructure comprising a network of interconnected nodes.

As noted, the training model could be implemented on a user interface. The interface could also be a point on introduction of data, such as training data or test data to compare to the trained model for analysis. The results of the comparison could then be shown on a user interface. The user interface could be the clinical device/tool itself, which can include a display or other interface to be used for the collection and review of the information obtained by the acoustic device.

A user interface is how the user interacts with a machine. The user interface can be a digital interface, a command-line interface, a graphical user interface ("GUI"), oral interface, virtual reality interface, or any other way a user can interact with a machine (user-machine interface). For example, the user interface ("UI") can include a combination of digital and analog input and/or output devices or any other type of UI input/output device required to achieve a desired level of control and monitoring for a device. Examples of input and/or output devices include computer mice, keyboards, touchscreens, knobs, dials, switches, buttons, speakers, microphones, LIDAR, RADAR, etc. Input(s) received from the UI can then be sent to a microcontroller to control operational aspects of a device.

The user interface module can include a display, which can act as an input and/or output device. More particularly, the display can be a liquid crystal display ("LCD"), a light-emitting diode ("LED") display, an organic LED ("OLED") display, an electroluminescent display ("ELD"), a surface-conduction electron emitter display ("SED"), a field-emission display ("FED"), a thin-film transistor ("TFT") LCD, a bistable cholesteric reflective display (i.e., e-paper), etc. The user interface also can be configured with a microcontroller to display conditions or data associated with the main device in real-time or substantially real-time.

Any components of the system could be connected via network or other communication protocol to transfer information, communicate with other systems, or provide other connectivity. In some embodiments, the network is, by way of example only, a wide area network ("WAN") such as a TCP/IP based network or a cellular network, a local area network ("LAN"), a neighborhood area network ("NAN"), a home area network ("HAN"), or a personal area network ("PAN") employing any of a variety of communication protocols, such as Wi-Fi, Bluetooth, ZigBee, near field communication ("NFC"), etc., although other types of networks are possible and are contemplated herein. The network typically allows communication between the communications module and the central location during moments of low-quality connections. Communications through the network can be protected using one or more encryption techniques, such as those techniques provided by the Advanced Encryption Standard (AES), which superseded the Data Encryption Standard (DES), the IEEE 802.1 standard for port-based network security, pre-shared key, Extensible Authentication Protocol ("EAP"), Wired Equivalent Privacy ("WEP"), Temporal Key Integrity Protocol ("TKIP"), Wi-Fi Protected Access ("WPA"), and the like.

For wired communications with a clinical device, it is envisioned that various protocols be used. For example, Ethernet could be used to transmit data from the clinical device to a remote location. Ethernet is a family of computer networking technologies commonly used in local area networks ("LAN"), metropolitan area networks ("MAN") and wide area networks ("WAN"). Systems communicating over Ethernet divide a stream of data into shorter pieces called frames. Each frame contains source and destination addresses, and error-checking data so that damaged frames can be detected and discarded; most often, higher-layer protocols trigger retransmission of lost frames. As per the OSI model, Ethernet provides services up to and including the data link layer. Ethernet was first standardized under the Institute of Electrical and Electronics Engineers ("IEEE") 802.3 working group/collection of IEEE standards produced by the working group defining the physical layer and data link layer's media access control ("MAC") of wired Ethernet. Ethernet has since been refined to support higher bit rates, a greater number of nodes, and longer link distances, but retains much backward compatibility. Ethernet has industrial application and interworks well with Wi-Fi. The Internet Protocol ("IP") is commonly carried over Ethernet and so it is considered one of the key technologies that make up the Internet.

Still other types of wired communication, as well as removable memory devices, could be used. For example, USB, micro-USB, USB-C, lightning, and the like, are all ways to transmit data, and can be used with any of the aspects and/or embodiments provided.

The invention claimed is:

1. A method of verifying effectiveness of a hearing aid device, comprising:

obtaining a wideband acoustic immittance-(WAI) measurement from an ear canal;

evaluating the WAI measurement with a trained machine learning network, wherein said machine learning network is trained by:

modeling a plurality of WAI measurements of users of a known age; and identifying classifiers of the model, wherein at least one of the classifiers comprises ear canal volume estimate in relation to WAI data;

wherein said evaluated WAI measurement comprises an immittance-predicted real-ear-to-coupler difference (RECD) of the ear canal that predicts the effectiveness of the hearing aid device in an ear without knowledge of impedance of the ear canal.

2. The method of claim 1, wherein the impedance-based measurement comprises 226 Hz tympanometry data measurement.

3. The method of claim 2, wherein the classifiers comprise:

a. static admittance; and b. age.

4. The method of claim 1, wherein steps of the training of the machine learning network further comprises using Bayesian statistical models.

5. The method of claim 1, further comprising implementing the trained machine learning network into a clinical apparatus used to obtain the acoustic measurement.

6. The method of claim 5, further comprising outputting the immittance-predicted RECD from the clinical apparatus.

7. The method of claim 6, wherein the step of outputting the immittance-predicted RECD from the clinical apparatus comprises:

a. displaying the output on the clinical apparatus; and/or b. communicating the output via a wired or wireless communication to a separate device to view the immittance-predicted RECD.

8. A system for verifying effectiveness of a hearing aid device, comprising:

a clinical device for obtaining a wideband acoustic immittance (WAI) measurement from an ear canal;

the device operatively connected to a computer readable medium configured to:

obtain the WAI measurement from the ear canal;

modeling the WAI measurement to obtain an estimated ear canal volume;

utilizing the estimated ear canal volume and an age to predict an immittance-based RECD.

9. The system of claim 8, wherein the WAI measurement comprises 226 Hz tympanometry data measurement.

10. The system of claim 9, wherein the modeling of the WAI measurement is used to obtain:

a. static admittance; and b. absorbance.

11. The system of claim 8, further comprising outputting the immittance-predicted RECD from the clinical device.

12. The system of claim 11, wherein the step of outputting the immittance-predicted RECD from the clinical device comprises:

a. displaying the output on the clinical device; and/or b. communicating the output via a wired or wireless communication to a separate device to view the immittance-predicted RECD.

13. A method for estimating the effectiveness of a hearing aid device, comprising:

obtaining WAI measurement from an ear canal;

modeling the WAI measurement; and using a machine-learned network to achieve an immittance-predicted RECD, wherein the machine-learned network is trained with a method comprising:

identifying classifiers of the modeled WAI measurement, wherein the classifiers comprise estimated ear canal volume;

combining the classifiers with a known age-based average real-ear-to-coupler difference (RECD); and statistically modeling the combination to result in the immittance-predicted RECD;

wherein the immittance-predicted RECD estimates the effectiveness of the hearing aid device.

* * * * *